US012653661B2

(12) United States Patent
Karapetian

(10) Patent No.: US 12,653,661 B2
(45) Date of Patent: Jun. 16, 2026

(54) OVAL STENT

(71) Applicant: Edwards Lifesciences Corporation, Irvine, CA (US)

(72) Inventor: Emil Karapetian, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 955 days.

(21) Appl. No.: 17/485,263

(22) Filed: Sep. 24, 2021

(65) Prior Publication Data

US 2022/0008188 A1     Jan. 13, 2022

Related U.S. Application Data

(63) Continuation of application No. PCT/US2020/024291, filed on Mar. 23, 2020.

(Continued)

(51) Int. Cl.
    *A61F 2/06*         (2013.01)
    *A61F 2/852*        (2013.01)
    (Continued)

(52) U.S. Cl.
    CPC ............... *A61F 2/06* (2013.01); *A61F 2/852* (2013.01); *A61F 2/90* (2013.01); *A61F 2/958* (2013.01); *A61F 2/966* (2013.01); *A61F 2002/0081* (2013.01); *A61F 2002/0086* (2013.01); *A61F 2002/067* (2013.01); *A61F 2002/068* (2013.01); *A61F 2002/8483* (2013.01); *A61F 2210/0004* (2013.01); *A61F 2210/0014* (2013.01); *A61F 2210/0076* (2013.01); *A61F 2230/0008* (2013.01); *A61F 2230/001* (2013.01); *A61F 2230/0015* (2013.01); *A61F 2250/001* (2013.01)

(58) Field of Classification Search
    CPC .... A61F 2/06; A61F 2/852; A61F 2/90; A61F 2/958; A61F 2/966; A61F 2/07; A61F 2250/0039; A61F 2/848; A61F 2/82; A61F 2/04; A61F 2230/0008; A61F 2230/001; A61F 2230/0015; A61F 2250/0018; A61F 2250/0014; A61F 2002/068

See application file for complete search history.

(56) References Cited

U.S. PATENT DOCUMENTS

| | | | |
|---|---|---|---|
| 5,997,563 A | 12/1999 | Kretzers | |
| 8,862,243 B2 * | 10/2014 | Gross ..................... A61N 1/326 607/116 |
| 9,271,825 B2 | 3/2016 | Arkusz et al. | |
| 9,386,991 B2 | 7/2016 | Gross | |

(Continued)

*Primary Examiner* — Dinah Baria
(74) *Attorney, Agent, or Firm* — Chang & Hale LLP

(57) ABSTRACT

A stent comprises an elastically deformable stent wall forming a lumen extending between a first opening and a second opening of the stent. The stent wall is configured to be percutaneously delivered into a blood vessel, secure to a blood vessel wall of a blood vessel, and radially expand from a first configuration to a second configuration within the blood vessel into direct contact with the blood vessel wall. The first configuration defines a first major dimension, a first minor dimension, a first cross-sectional area, a first cross-sectional shape, and a first perimeter of the stent wall. The second configuration defines a second major dimension, a second minor dimension that is greater than the first minor dimension, a second cross-sectional area that is greater than the first cross-sectional area, and the first perimeter of the stent wall.

42 Claims, 14 Drawing Sheets

Related U.S. Application Data

(60) Provisional application No. 62/825,686, filed on Mar. 28, 2019.

(51) Int. Cl.

| | |
|---|---|
| *A61F 2/90* | (2013.01) |
| *A61F 2/958* | (2013.01) |
| *A61F 2/966* | (2013.01) |
| *A61F 2/00* | (2006.01) |
| *A61F 2/848* | (2013.01) |

(56) References Cited

U.S. PATENT DOCUMENTS

| | | | |
|---|---|---|---|
| 2006/0089704 A1 | 4/2006 | Douglas | |
| 2007/0167955 A1* | 7/2007 | Arnault De La Menardiere | A61F 2/852 |
| | | | 623/1.11 |
| 2007/0287879 A1* | 12/2007 | Gelbart | A61B 17/12022 |
| | | | 600/16 |
| 2008/0033501 A1* | 2/2008 | Gross | A61N 1/36017 |
| | | | 607/44 |
| 2009/0118811 A1 | 5/2009 | Moloney | |
| 2009/0198315 A1* | 8/2009 | Boudjemline | D04C 3/48 |
| | | | 623/1.2 |
| 2009/0312834 A1* | 12/2009 | Wood | A61F 2/90 |
| | | | 623/1.15 |
| 2011/0118773 A1 | 5/2011 | Gross et al. | |
| 2012/0150274 A1* | 6/2012 | Shalev | A61F 2/954 |
| | | | 623/1.12 |
| 2016/0310299 A1* | 10/2016 | Mangiardi | A61F 2/844 |
| 2017/0151051 A1* | 6/2017 | Kang | A61F 2/04 |
| 2018/0085215 A1 | 3/2018 | Vaturi et al. | |
| 2019/0069903 A1* | 3/2019 | Deshmukh | A61B 17/12109 |
| 2019/0175374 A1* | 6/2019 | Park | A61F 2/07 |
| 2020/0179095 A1* | 6/2020 | Schulick | A61F 2/856 |

* cited by examiner

OVAL STENT

RELATED APPLICATION

This application is a continuation application of International Patent Application Serial No. PCT/US2020/024291, filed Mar. 23, 2020 and entitled OVAL STENT, which claims priority to U.S. Provisional Application No. 62/825,686, filed Mar. 28, 2019, and entitled OVAL STENT, the complete disclosures of both of which are hereby incorporated by reference in their entireties.

BACKGROUND

The present disclosure generally relates to vascular repair, and, more particularly, to methods and apparatuses using an oval stent to restore vascular compliance.

Catheter systems, such as treatment, delivery, and/or deployment catheters, can be used to treat patients internally. For example, delivery catheter systems can be used to deliver and deploy prosthetic devices, such as prosthetic heart valves, at locations inside the body. Prosthetic heart valves can be delivered to a treatment site (e.g., aortic, mitral, tricuspid, and/or pulmonary valve position) within a patient using transcatheter techniques.

SUMMARY

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

Some implementations of the present disclosure relate to a stent comprising a stent wall defining an elongated tubular member. The elongated tubular member comprises a first end with a first opening, a second end with a second opening, a lumen extending between the first opening and the second opening, and a stent length extending between the first end and the second end, wherein the stent wall is an open cell wall and is adapted to be secured to a blood vessel wall of a blood vessel. The lumen comprises a cross-sectional shape, a cross-sectional area, a major dimension, a minor dimension, and a perimeter. The stent is elastically deformable between a first configuration and a second configuration, wherein the stent is biased toward the first configuration, wherein in the first configuration the major dimension is a first major dimension, the minor dimension is a first minor dimension, and the cross-sectional area is a first cross-sectional area. In the second configuration, the major dimension is a second major dimension, the minor dimension is a second minor dimension, and the cross-sectional area is a second cross-sectional area. The first minor dimension is less than the second minor dimension, and wherein the first cross-sectional area is smaller than the second cross-sectional area. The stent is adapted to be percutaneously delivered to the blood vessel in a compressed configuration and radially expanded within the blood vessel and into direct contact with the blood vessel wall.

The first major dimension may be greater than the second major dimension. In some embodiments, in the first configuration, the cross-sectional shape comprises an oval shape. In the first configuration, the cross-sectional shape may comprise a peanut shape. In some embodiments, in the first configuration, the cross-sectional shape comprises a kidney shape. The stent may be at least partially composed of Nitinol. In some embodiments, the stent further comprises barbs extending radially outwardly from the stent wall. The stent may be adapted to be radially expanded into contact with an aortic wall of an aorta, and/or the perimeter of the lumen may approximate a perimeter of the aorta. In some embodiments, at least a portion of the stent wall is adapted to be endothelialized into the blood vessel wall.

In some embodiments, the stent wall comprises a first stent layer and a second stent layer, wherein the first stent layer and the second stent layer comprise a single continuous layer of open-celled material, and the second stent layer is folded within the first stent layer such that the first stent layer comprises an outer layer of the stent wall. The stent wall may comprise a third stent layer, wherein the first stent layer and the second stent layer and the third stent layer may comprise a single continuous layer of open-celled material, and the third stent layer may be folded within the second stent layer such the third stent layer comprises an inner layer and the second stent layer may be positioned between the first stent layer and the third stent layer.

The stent may be adapted to be physically held in the first configuration or in the second configuration after being radially expanded within the blood vessel and into direct contact with the blood vessel wall. In some embodiments, the stent further comprises a tension line adapted to physically hold the stent in the first configuration or in the second configuration. The tension line may be adapted to be dissolvable within blood of a patient. In some embodiments, the tension line is adapted to be percutaneously removed from the stent by a user such as an interventional cardiologist.

Some implementations of the present disclosure relate to a system for providing compliance to a native blood vessel. The system comprises a catheter comprising a catheter distal portion, a catheter proximal portion, and an elongate catheter body extending from the catheter distal portion to the catheter proximal portion, wherein the catheter is adapted for the catheter distal portion to be percutaneously advanced within a patient's vasculature to the native blood vessel. The system further comprises a stent comprising a stent wall defining an elongated tubular member, the elongated tubular member comprising a first end with a first opening, a second end with a second opening, a lumen extending between the first opening and the second opening, and a stent length extending between the first end and the second end, wherein the stent wall is an open cell wall and is adapted to be secured to a blood vessel wall of a blood vessel. The lumen comprises a cross-sectional shape, a cross-sectional area, a major dimension, a minor dimension, and a perimeter. The stent is elastically deformable between a first configuration and a second configuration, wherein the stent is biased toward the first configuration, wherein in the first configuration the major dimension is a first major dimension, the minor dimension is a first minor dimension, and the cross-sectional area is a first cross-sectional area; and wherein in the second configuration the major dimension is a second major dimension, the minor dimension is a second minor dimension, and the cross-sectional area is a second cross-sectional area; wherein the first minor dimension is less than the second minor dimension, and wherein the first cross-sectional area is smaller than the second cross-sectional area. The stent is adapted to be percutaneously delivered to the blood vessel in a compressed configuration and radially expanded within the blood vessel and into direct contact with the blood vessel wall. The stent is releasably secured to the catheter distal portion.

The catheter distal portion may comprise an expandable balloon adapted to radially expand the stent into contact with a blood vessel wall of the native blood vessel. In some embodiments, the catheter distal portion comprises a retractable sheath adapted to hold the stent in a radially compressed configuration to the stent distal portion.

Some implementations of the present disclosure relate to a device for providing compliance within a blood vessel. The device comprises a distal stent, wherein the distal stent in an expanded configuration comprises a distal stent lumen and a distal stent cross-sectional area, wherein the distal stent comprises a distal stent wall having an open cell configuration adapted to directly engage a blood vessel wall of a blood vessel and to permit blood to flow from the distal stent lumen to the blood vessel wall. The device further comprises a proximal stent, wherein the proximal stent in an expanded configuration comprises a proximal stent lumen and a proximal stent cross-sectional area, wherein the proximal stent comprises a proximal stent wall having an open cell configuration adapted to directly engage the blood vessel wall and to permit blood to flow from the proximal stent lumen to the blood vessel wall. The device further comprises a middle stent positioned between the distal stent and the proximal stent, the middle stent formed from a memory material and forming a middle stent lumen, wherein the middle stent is elastically deformable between a first configuration and a second configuration, wherein the middle stent is biased toward the first configuration, wherein in the first configuration the middle stent lumen comprises a first cross-sectional shape, a first cross-sectional area, a first major dimension, and a first minor dimension, wherein the first minor dimension is less than the first major dimension, wherein the first cross-sectional area is less than the distal stent cross-sectional area and also less than the proximal stent cross-sectional area. The device further comprises a lining extending between the distal stent and the proximal stent and along a middle stent wall of the middle stent portion, the lining adapted to prevent the flow of blood therethrough.

In the second configuration, the middle stent lumen may comprise a second cross-sectional shape, a second cross-sectional area, a second major dimension, and a second minor dimension, wherein the first minor dimension may be less than the second minor dimension. In some embodiments, the distal and proximal stents are adapted to be radially expanded into contact with an aortic wall of an aorta, and wherein the second cross-sectional area of the middle stent lumen approximates a cross-sectional area of the aorta. The first major dimension may be greater than the second major dimension.

In some embodiments, the distal and proximal stents are formed from a plastically-deformable material. The distal and proximal stents may be formed from stainless steel or a cobalt alloy, and the middle stent is formed from Nitinol. In some embodiments, the first cross-sectional shape comprises an oval shape. The first cross-sectional shape may comprise a peanut shape. In some embodiments, the first cross-sectional shape comprises a kidney shape.

Some implementations of the present disclosure relate to a method of restoring compliance to a blood vessel. The method comprises providing a system comprising a delivery catheter and a stent, wherein the delivery catheter comprises a catheter distal portion, a catheter proximal portion, and a catheter elongated body, wherein the delivery catheter is adapted to be advanced into a patient's vasculature to position the catheter distal portion within a desired blood vessel The stent comprises a stent wall defining an elongated tubular member, the elongated tubular member comprising a first end with a first opening, a second end with a second opening, a stent lumen extending between the first opening and the second opening, and a stent length extending between the first end and the second end, wherein the stent wall is an open cell wall and is adapted to be secured to a blood vessel wall of a blood vessel. The stent is elastically deformable between a first configuration and a second configuration, wherein the stent is biased toward the first configuration. In the first configuration, the stent lumen comprises a first major dimension, a first minor dimension, a first cross-sectional shape, and a first cross-sectional area. In the second configuration, the stent lumen comprises a second major dimension, a second minor dimension, a second cross-sectional shape, and a second cross-sectional area. The first minor dimension is less than the second minor dimension, and wherein the first cross-sectional area is smaller than the second cross-sectional area. The method further comprises advancing the catheter distal portion through a patient's vasculature to the desired blood vessel, positioning the catheter distal portion at a desired treatment site in the desired blood vessel, radially expanding the stent into contact with the blood vessel wall at the desired treatment site, and removing the catheter distal portion from the patient's vasculature.

In some embodiments, the catheter distal portion comprises an expandable balloon, wherein radially expanding the stent comprises expanding the expandable balloon. When the catheter distal portion is advanced through the patient's vasculature, the stent may be positioned on the expandable balloon. The catheter distal portion may comprise a sheath slidingly positioned over the stent, wherein when the catheter distal portion is advanced through the patient's vasculature the sheath is positioned over the stent.

After radially expanding the stent into contact with the blood vessel wall at the desired treatment site, the stent may be physically held by a restraint in the first configuration or in the second configuration. In some embodiments, the method further comprises, after removal of the delivery catheter from the patient, releasing the restraint from the stent so that the stent is no longer held in the first configuration or in the second configuration, and can deform between the first configuration and the second configuration. The restraint may comprise a tension line, and wherein releasing the restraint comprises cutting and removing the tensioning line. In some embodiments, the restraint comprises an absorbable tension line, and wherein releasing the stent occurs responsive to exposure of the absorbable tension line to blood of the patient.

Some implementations of the present disclosure relate to a device for restoring blood vessel compliance. The device comprises a primary stent body comprising a primary stent wall defining an elongated tubular member, the elongated tubular member comprising a first end with a first opening, a second end with a second opening, a primary stent lumen extending between the first opening and the second opening, and a primary stent length extending between the first end and the second end; wherein the primary stent lumen comprises a cross-sectional shape, a cross-sectional area, a major dimension, a minor dimension, and a perimeter; wherein the primary stent body is elastically deformable between a first configuration and a second configuration, wherein the primary stent body is biased toward the first configuration, wherein in the first configuration the major dimension is a first major dimension, the minor dimension is a first minor dimension, and the cross-sectional area is a first cross-sectional area; and wherein in the second configuration the major dimension is a second major dimension, the minor dimension is a second minor dimension, and the cross-sectional area is a second cross-sectional area; wherein the first minor dimension is less than the second minor dimension, and wherein the first cross-sectional area is smaller than the second cross-sectional area; wherein the primary stent body is adapted to be percutaneously delivered to the main blood vessel in a compressed configuration and radially expanded within the main blood vessel and into direct contact with the main blood vessel wall. The device further comprises one or more anchors extending from the primary stent body, where each of the one or more anchors is adapted to be deployed into engagement with tissue of a branch blood vessel, wherein the branch blood vessel branches away from and has a smaller diameter than the main blood vessel.

In some embodiments, at least one of the one or more anchors extends from the primary stent body at a position between the first end and the second end of the primary stent body. At least one of the one or more anchors may be adapted to be deployed into contact with walls of a renal artery. In some embodiments, at least one of the one or more anchors extends from a first end of the primary stent body. At least one of the one or more anchors may be adapted to be deployed into contact with walls of an iliac artery.

At least one of the one or more anchors may comprise a wireform adapted to pass within a branch blood vessel and adapted to engage wall tissue of the branch blood vessel. The wireform may be formed from a memory material. In some embodiments, at least one of the one or more anchors comprises an anchor stent body, the anchor stent body comprising an anchor stent wall defining an anchor stent lumen, wherein the anchor stent body is adapted to be radially expanded into contact with a wall of a branch blood vessel. The anchor stent body may be formed from a memory material and is biased toward a configuration wherein the anchor stent lumen comprises a cross-sectional shape which is an oval, peanut, or kidney shape. In some embodiments, the anchor stent body comprises an anchor stent body length in the range from 0.5 and 7 cm.

It should be understood that each of the elements disclosed herein can be used with any and all of the elements disclosed herein, even though the specific combination of elements may not be explicitly shown in the figures herein. In other words, based on the explanation of the particular device, one of skill in the art should have little trouble combining the features of certain of two such devices. Therefore, it should be understood that many of the elements are interchangeable, and the invention covers all permutations thereof.

Other objects, features, and advantages of the present invention will become apparent from a consideration of the following detailed description.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

In humans and other vertebrate animals, blood circulation throughout the body is facilitated by a blood circulatory system comprising various arteries, capillaries, veins, and coronary vessels, which work together with the heart to supply blood to the various regions of the body. The heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.). The valves may permit fluid flow between the heart and the various arteries of the cardiovascular system.

Figure 1:
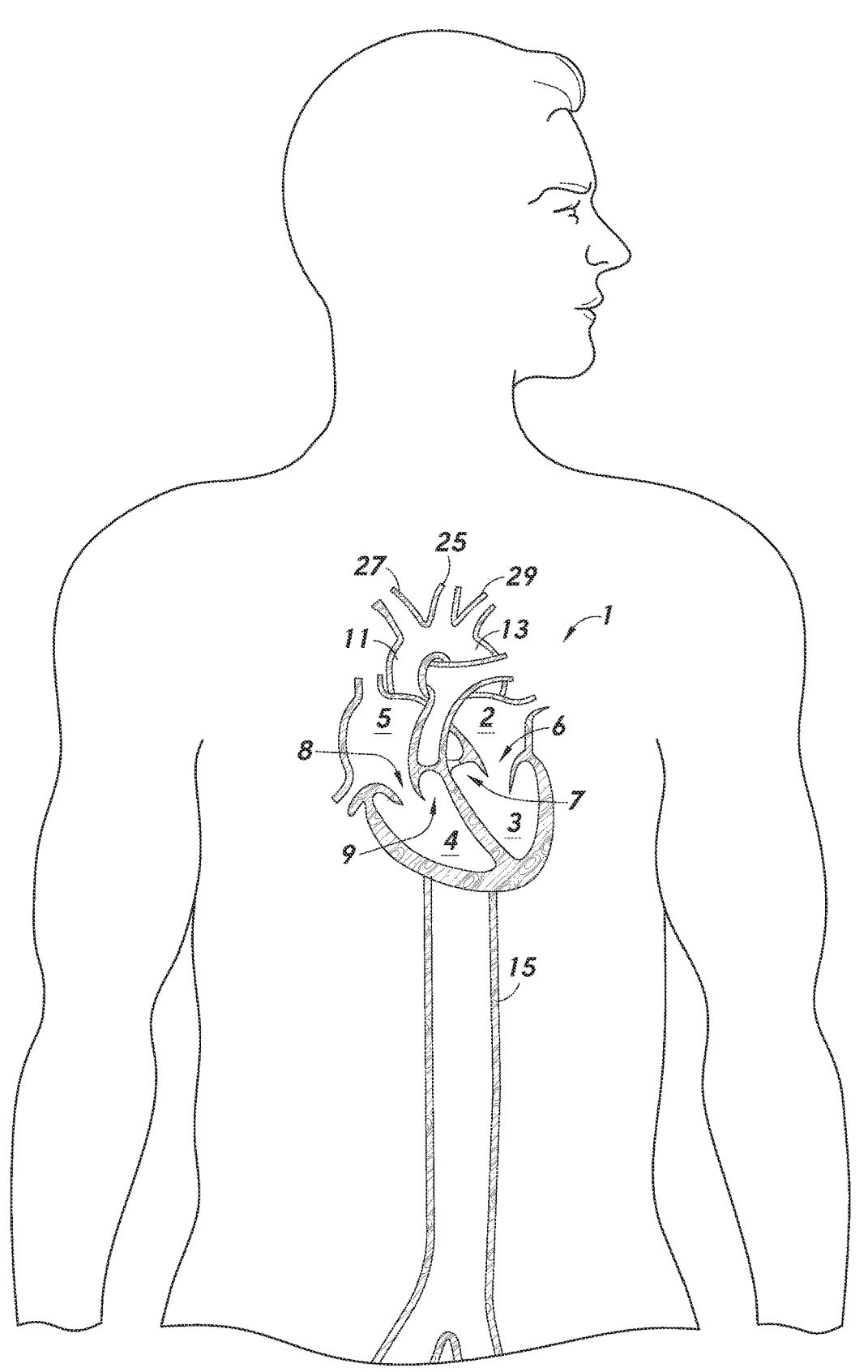
FIG. 1 illustrates an example representation of a heart and associated vessels having various features relevant to certain embodiments of the present inventive disclosure.

FIG. 1 illustrates an example representation of a heart 1 and associated artery 15 having various features relevant to certain embodiments of the present inventive disclosure. The heart 1 includes four chambers, namely the left atrium 2, the left ventricle 3, the right ventricle 4, and the right atrium 5. The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (i.e., systole) and open during ventricular expansion (i.e., diastole). The valves of the heart 1 further include the pulmonary valve 9, which separates the right ventricle 4 from the pulmonary artery, and may be configured to open during systole so that blood may be pumped toward the lungs, and close during diastole to prevent blood from leaking back into the heart from the pulmonary artery. The pulmonary valve 9 generally has three cusps/leaflets (not shown). The heart 1 further includes the mitral valve 6, which generally has two cusps/leaflets (not shown) and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 11. The aortic valve 7 is configured to open during systole to allow blood leaving the left ventricle 3 to enter the aorta 11, and close during diastole to prevent blood from leaking back into the left ventricle 3.

The aorta is coupled to the heart via the aortic valve 7, wherein the ascending aorta 11 arises from the heart 1 and gives rise to the innominate artery 27, the left common carotid artery 25, and the left subclavian artery 29 before continuing as the descending thoracic aorta 13 and further the abdominal aorta 15.

Arteries, such as the aorta 15, may utilize arterial compliance to store and release energy through the stretching of blood vessel walls. As described herein, arterial "compliance" may refer to the ability of an arterial blood vessel to distend and increase in volume with increasing transmural pressure, or the tendency of an artery, or portion thereof, to resist recoil toward its original dimensions on application of a distending or compressing force.

In a normal compliant blood vessel, volume expansion and contraction occur by the stretching and retraction of the blood vessel walls responsive to heart beats. Aging, hypertension and other factors may result in decreased elasticity in blood vessel walls in the vascular system, leading to decreased vascular compliance. Such decreased vascular compliance (also called arterial stiffness or vascular stiffness) may result in minimal volume change during the diastolic to systolic pressure change. Depending on where the decreased vascular compliance occurs, the patient's health can be impaired. Loss of compliance in the aorta 15, for example, can lead to increased pulse pressure (e.g., increased systolic pressure and/or decreased diastolic pressure) and can result in increased left ventricle workload (and/or decreased cardiac efficiency). The loss in aortic compliance can also have a detrimental effect on coronary perfusion. Treatment to improve vascular compliance restoration can include the addition of a compliant chamber that attaches to the vascular system, with the compliant chamber providing added compliance. Such chambers may introduce challenges, such as thrombosis and fatigue issues.

The present invention provides systems, devices, and methods for restoring compliance to non-compliant vascular structures by causing temporary changes in the cross-sectional geometry of a blood vessel without changing or with minimal change to a peripheral wall length of the blood vessel during initial implant. More specifically, the relaxed/ diastolic cross-sectional shape of the blood vessel may be altered into a non-circular shape and/or, when subjected to increased pressure (e.g., during systole), the blood vessel may assume a circular (or more circular) shape. Because a highest area-to-periphery ratio may be achieved with a circular shape, a device which provides for transition between a non-circular shape and a circular (or more circular) shape may allow for cross-sectional area expansion. Accordingly, some embodiments herein may allow for expansion/contraction of the blood vessel cross-sectional area between diastole/systole without the need for high elasticity of the blood vessel walls.

Some embodiment systems may comprise an elastic spring-like device that can distort (e.g., via pushing, pulling, etc.) the cross-sectional shape of the blood vessel to a cross-sectional shape that may have a smaller cross-sectional area at diastole (i.e., during the lower applied pressure). At systole (i.e., during the higher applied pressure), the elastic device can expand or otherwise flex to increase the cross-sectional area of the blood vessel (e.g., via change in blood vessel and/or device geometry but with little or no change in blood vessel and/or device perimeter) to provide the desired added compliance.

In some embodiments, a stent and/or similar device may provide an added compliance (i.e., added change in volume over a constant change in pressure) to any blood vessel in or on which it is placed. The term "stent" is used herein in accordance with its broad and ordinary meaning and may refer to any device configured to be implanted in a blood vessel for improving compliance of the blood vessel. Such added compliance can benefit any part of a pulsatile flow system that may suffer from increased systolic pressures (e.g., hypertension). Some embodiment devices may be configured to shift systolic flow to diastolic flow with a constant cardiac output (e.g., yielding increased cardiac efficiency), which may be highly beneficial in the aorta and/or for coronary perfusion. Examples of blood vessels that can benefit from added compliance can include the aorta, pulmonary arteries, and/or the superior/inferior vena cava.

In some embodiments, a flexible stent and/or other implant may be used to reshape a non-compliant/non-elastic blood vessel into a non-circular shape when in the diastolic/ relaxed/biased condition. The non-circular shape may include an oval, triangle, peanut, figure-8, etc. The stent and/or other implant may be configured to be biased toward the non-circular shape and/or may be capable of deforming to a circular/more circular shape (and thus a larger cross-sectional area) in response to pressure. For example, blood flow through a non-compliant/non-elastic blood vessel may be capable of causing deformation of a stent and/or similar device described herein. The perimeter of the non-circular shape may be identical or similar to the more circular shape. In this way, the stent and blood vessel may maintain the same perimeter and/or have minimal change in perimeter while changing shape in response to blood flow changes. In some embodiments, the non-circular shape may have a smaller cross-sectional area than the more circular shape. When the heart beats, the blood vessel may be deformed into a more circular shape, after which the stent/implant may be configured to press and/or pull the blood vessel back toward the more non-circular shape. In this manner, the stent/ implant may be configured to restore some compliance to the otherwise non-compliant blood vessel.

In some embodiments, a stent may be deployed within a blood vessel. However, one or more stents may additionally or alternatively be configured to be positioned around an outer surface of the blood vessel. A stent may comprise one or more hooks and/or other attachment mechanisms adapted to help secure the stent to the tissue of the blood vessel wall.

A stent may comprise a stent wall defining an elongated tubular member having a first end with a first opening. The tubular member may further comprise a second end with a second opening, a lumen extending between the first opening and the second opening, and/or a stent length extending between the first end and the second end. The stent wall may comprise an open cell wall and/or may be adapted to be secured to a blood vessel wall of a blood vessel, such as via outward-directed hooks and/or endothelialization. The stent wall and/or a lumen at least partially surrounded by the stent wall may be configured to form a cross-sectional shape, a cross-sectional area, a major dimension, and/or a minor dimension. The stent may be elastically deformable between a first configuration and a second configuration, with the stent biased toward the first configuration. The first configuration may define various characteristics of the stent, for example the major dimension may be a first major dimension, the minor dimension may be a first minor dimension, the cross-sectional area may be a first cross-sectional area, and the cross-sectional shape may be a first cross-sectional shape. The second configuration may define various characteristics of the stent, for example, the major dimension may be a second major dimension, the minor dimension may be a second minor dimension, the cross-sectional area may be a second cross-sectional area, and the cross-sectional shape may be a second cross-sectional shape. The first minor dimension may be less than the second minor dimension, the first major dimension may be greater than the second major dimension, and/or the first cross-sectional area may be smaller than the second cross-sectional area.

In some embodiments, one or more stents may be at least partially composed of a shape-memory material, such as Nitinol. Stents may be configured to be biased toward a first cross-sectional shape. The first cross-sectional shape may be any shape, including an oval, triangle, peanut, figure-8, and/or kidney shape.

A stent may be configured to be percutaneously delivered to a blood vessel in a compressed configuration. Once within the blood vessel, the stent and/or stent wall of the stent may be configured to be radially expanded into direct surface contact with the blood vessel wall (e.g., the aortic wall of an aorta). In some embodiments, the stent may be configured to be expanded such that the perimeter of a lumen of the stent may approximate and/or exceed a perimeter of the blood vessel at least prior to expansion of the stent. In some cases, a stent configured to expand to an at least slightly greater perimeter than the native blood vessel may provide improved traction and/or resistance to migration within the blood vessel. Moreover, the stent having a perimeter approximate to and/or greater than the blood vessel may increase and/or ensure positive engagement with the blood vessel and/or to maximize a compliance effect. The stent wall and/or a portion of the stent wall may be configured to be endothelialized into the blood vessel wall. In some embodiments, the blood vessel may be an aorta, and/or the second cross-sectional area of the lumen may approximate a cross-sectional area of the aortic section in which the stent is deployed.

In some embodiments, a stent may be formed from multiple layers. For example, the stent wall may comprise at least a first stent layer and a second stent layer. The first stent layer and the second stent layer may be formed from a single continuous layer of open-celled material, with the second stent layer folded within the first stent layer such that the first stent layer may comprise an outer layer of the stent wall with the second stent layer configured to be situated inside and/or beneath the first stent layer. In some embodiments, the stent wall may comprise third, fourth, and/or more stent layers. The various stent layers may each be folded within the others. For example, a first stent layer, a second stent layer, and a third stent layer may form and/or be formed from a single continuous layer (e.g., a continuous layer of open-celled material). The second stent layer may be folded within the first stent layer, with the third stent layer folded within the second stent layer such the third stent layer comprises an inner layer and the second stent layer is configured to be positioned between the first stent layer and the third stent layer. The various layers may be secured to each other via different materials (e.g., different from the materials of the respective layers), such as cloth, wire, suture, etc. The various layers may be configured to be pre-assembled prior to deployment and/or may be configured to be delivered into the patient separately and/or assembled in situ to form a particular device.

A stent may be adapted to be physically held in a particular configuration after radial expansion of the stent and/or stent wall within the blood vessel and into direct contact with the blood vessel wall, which can provide time for the stent to be secured to the blood vessel wall, e.g., via endothelialization. For example, a stent may comprise and/or may be configured to attach to a tension line which may be configured to physically hold the stent in a specific desired configuration, such as where the tension line is adapted to restrain the stent major dimension or minor dimension to a desired size (e.g., holding the stent in a more oval shape or in a more circular shape). The tension line may be configured to be dissolvable within blood of a patient. The tension line may be configured to be percutaneously removed from the stent by a user such as an interventional cardiologist.

Some systems described herein for providing compliance to a native blood vessel may include a catheter and/or an implant such as a stent. The catheter may comprise a catheter distal portion, a catheter proximal portion, and/or an elongate catheter body extending from the catheter distal portion to the catheter proximal portion. In some embodiments, the catheter may be adapted for the catheter distal portion to be percutaneously advanced within a patient's vasculature to a blood vessel. The catheter distal portion may comprise an expandable balloon adapted to radially expand the stent into contact with the blood vessel wall. The catheter distal portion may comprise a retractable sheath adapted to prevent radial expansion of the stent. For example, the catheter distal portion may be configured to prevent the stent from expanding from a first (e.g., compressed) configuration to a second (e.g., expanded) configuration.

Some embodiment devices may include hybrid/composite structures, such as devices having stents adapted to secure the device within the patient's vasculature, combined with self-expanding/biased stents for deforming between smaller and larger cross-sectional areas responsive to blood pressure as the heart beats. For example, a device may comprise a distal stent which, in an expanded configuration, may comprise a distal stent lumen and distal stent cross-sectional area. The distal stent may comprise a distal stent wall with an open cell configuration adapted to directly engage a blood vessel wall of the blood vessel and/or to permit blood to flow from the distal stent lumen to the blood vessel wall. The device may also comprise a proximal stent of similar configuration to the distal stent, such as having an expanded configuration with a proximal stent lumen and a proximal stent cross-sectional area, and/or comprising a proximal stent wall having an open cell configuration adapted to directly engage the blood vessel wall and to permit blood to flow from the proximal stent lumen to the blood vessel wall. The device may further include a middle stent configured to be positioned between the distal stent and the proximal stent, the middle stent formed from a memory material and forming a middle stent lumen. The middle stent may be configured to be elastically deformable between a first configuration and a second configuration, and/or may be configured to be biased toward the first configuration, wherein in the first configuration the middle stent and/or middle stent lumen may comprise a first cross-sectional shape, a first cross-sectional area, a first major dimension, and a first minor dimension. The first minor dimension may be less than the first major dimension and/or the first cross-sectional area may be less than the distal stent cross-sectional area and/or less than the proximal stent cross-sectional area. The device may comprise a lining extending between the distal stent and the proximal stent and along a middle stent wall of the middle stent portion. The lining may be adapted to prevent the flow of blood therethrough.

In the second configuration, the middle stent and/or middle stent lumen may have a second cross-sectional shape, a second cross-sectional area, a second major dimension, and/or a second minor dimension, with the first minor dimension being less than the second minor dimension. The first major dimension may be less than the second major dimension. The distal and proximal stents may be adapted to be radially expanded into contact with a blood vessel wall such as an aortic wall of an aorta. The second cross-sectional area of the lumen may approximate a cross-sectional area of the aorta.

The distal and proximal stents may be at least partially composed of a plastically-deformable material, such as stainless steel or a cobalt alloy, yielding a more circular cross-section. The middle stent may be at least partially composed of a shape-memory material (e.g., Nitinol). The first cross-sectional shape of the middle stent may have any shape, for example an oval, triangle, kidney, peanut, and/or figure-8 shape.

Some embodiments may relate to methods for restoring compliance to a blood vessel. A method may include providing a system comprising a delivery catheter and/or a stent, with the delivery catheter having a catheter distal portion, a catheter proximal portion, and a catheter elongated body. The delivery catheter may be adapted to be advanced into a patient's vasculature to position the catheter distal portion within a desired blood vessel. The stent may be any implant as disclosed herein. The method may involve advancing the catheter distal portion through a patient's vasculature to the desired blood vessel, positioning the catheter distal portion at a desired treatment site in the desired blood vessel, radially expanding the stent into contact with the blood vessel wall at the desired treatment site, and/or removing the delivery catheter from the patient's vasculature. The catheter distal portion may comprise an expandable balloon, wherein radially expanding the stent may involve expanding the balloon. The stent may be configured to be positioned on the expandable balloon when the catheter distal portion is advanced through the patient's vasculature. The catheter distal portion may comprise a sheath configured to slide at least partially over the stent, such that when the catheter distal portion is advanced through the patient's vasculature, the sheath may be configured to be positioned at least partially over the stent.

After radially expanding the stent into contact with the blood vessel wall at the desired treatment site, the stent may be configured to be physically held by a restraint in a desired configuration, such as being held in the first configuration or in the second configuration. After removal of the delivery catheter from the patient (e.g., including hours or days later and/or after the stent has been endothelialized or otherwise secured to the blood vessel wall), the restraint can be released from the stent so that the stent may be no longer held in the first or second configuration and/or can adopt either configuration and deform between the configurations. In some embodiments, the restraint may comprise a tension line. Releasing the restraint may involve cutting and/or removing the tension line. The tension line may be absorbable, and releasing the stent from the restraint may be configured to occur responsive to exposure of the absorbable tension line to blood of the patient. The absorbable tension line may be adapted to be absorbed over sufficient time such that the stent may be endothelialized or otherwise secured to the blood vessel wall before the absorbable tension line is absorbed and the stent is released from the restraint.

A stent may comprise a tubular/cylindrical shape, a simple hoop, a C-shaped clip/clamp, and/or a spring-like mechanism. In some embodiments, a stent may be at least partially composed of a shape-memory material such as Nitinol, which may allow the stent to deform to cause the blood vessel to assume a circular shape when subjected to external forces (e.g., forces caused by blood flow) and then return to a non-circular shape to reduce the blood vessel cross-sectional area.

In some embodiments, a stent may be at last partially self-expanding, such as where formed from a memory material such as Nitinol. The stent may be configured to be delivered via catheter to a desired position in, around, or adjacent the blood vessel. The catheter may comprise an expandable balloon to aid in deployment of the stent into firm initial contact with the blood vessel, such as where the balloon expands the stent to a deployment size/diameter larger than its programmed/biased condition. The deployment size/diameter may even be larger than the expanded size/diameter that the stent may later achieve when expanded due to blood flow/heartbeat. This deployment size/diameter may be sufficient to embed or otherwise secure the stent to the blood vessel wall. In some embodiments, the stent can be at least partially open-celled, such as to avoid blocking branch vessels. Whereas in another embodiment, the stent can be completely covered, such as to isolate the aorta or other blood vessels from fluid pressure (e.g., regions of aneurysms, or compromised vessel walls).

Stents may comprise barbs and/or other attachment mechanisms which can prevent migration and/or can help hold the stent securely to a blood vessel wall in order to cause the blood vessel cross-sectional shape to change responsive to the stent shape change. Such barbs and/or other attachment devices may be adapted to engage the wall of the blood vessel in which the stent is deployed.

In some embodiments, a stent may comprise one or more anchors extending from the main stent body (such as any of the main stent bodies disclosed herein). Each of the one or more anchors may be adapted to be deployed into engagement with tissue of a branch blood vessel or other vascular structure, such as where a branch blood vessel branches away from the main blood vessel. The branch blood vessel may have a diameter that may be smaller than the diameter of the main blood vessel in which the main stent body is deployed. One or more of the anchors may extend from the main stent body at a position between the first end and the second end of the main stent body, or from the first end or from the second end of the main stent body. One or more of the anchors may be adapted to be deployed into contact with walls of a renal artery, or into the walls of an iliac artery. One or more of the anchors may comprise a wireform (e.g., formed from a shape-memory material) and/or may be adapted to pass within the branch blood vessel and/or adapted to engage the wall tissue of the branch blood vessel such as an iliac or renal artery. One or more of the anchors may comprise an anchor stent body with an anchor stent wall defining an anchor stent lumen, and/or the anchor stent body may be adapted to be radially expanded into contact with a wall of a branch blood vessel such as an iliac or renal artery. The anchor stent body may be at least partially composed of a shape-memory material and/or may be biased toward a configuration wherein the anchor stent lumen comprises a cross-sectional shape which is non-circular (e.g., an oval, triangle, peanut, or kidney shape). In some embodiments, the anchor stent body may have an overall length in the range from 0.5 and 7 cm.

In some embodiments, a system including one or more stents as described herein may be used for endovascular repair (e.g., Abdominal Aortic Aneurysm (AAA) endovascular repair). For example, a catheter may be inserted into a blood vessel of a patient to deliver a stent at or near an aneurysm. The stent may be configured to act as a graft and/or may be configured to expand and/or to deform from a less circular shape to a more circular shape within the vessel to form a more stable channel for blood flow.

The systems, devices, and/or methods described herein can be utilized in various catheter-based procedures, including minimally-invasive procedures and percutaneous procedures. In some embodiments the methods/systems/devices may involve trans-aortic deliveries through a small chest (or abdominal) incision. In other embodiments, the methods/systems/devices can be used in minimally invasive surgical procedures. In yet other embodiments, the methods/systems/devices can be used in percutaneous procedures, such as via a catheter or catheters into the patient's arterial system (e.g., through the femoral or brachial arteries).

Figure 2A:
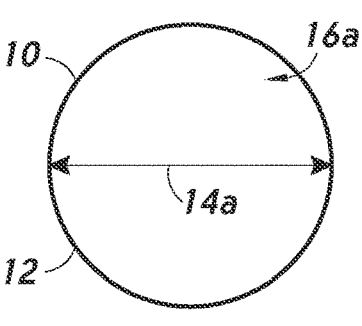
FIGS. 2A and 2B depict a blood vessel having a blood vessel wall that is elastic.
Figure 2B:
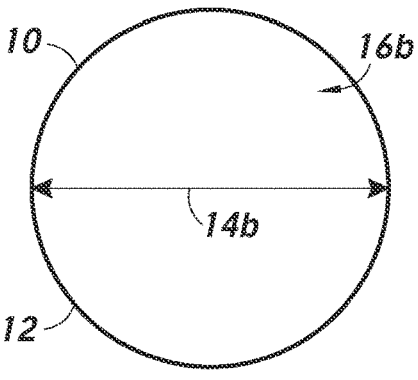

FIGS. 2A and 2B depict a blood vessel 10 having a blood vessel wall 12 that is elastic. The blood vessel 10 in diastolic pressure (FIG. 2A) may have a relatively small diameter 14a and cross-sectional area 16a, but in systolic pressure (FIG. 2B), the blood vessel wall 12 stretches so that the blood vessel 10 assumes a larger diameter 14b and cross-sectional area 16b.

Figure 3A:
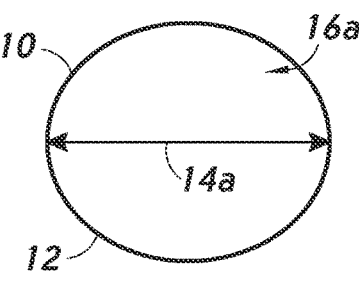
FIGS. 3A and 3B depict a blood vessel having a blood vessel wall that is inelastic and/or has lost elasticity.
Figure 3B:
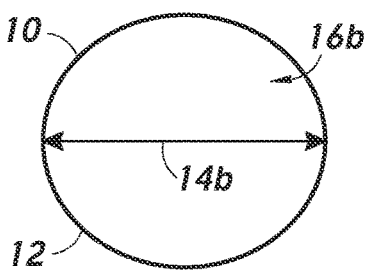

FIGS. 3A and 3B depict a blood vessel 10 having a blood vessel wall 12 that is inelastic and/or has lost elasticity. The diastolic diameter 14a and/or diastolic cross-sectional area 16a (FIG. 3A) may be only slightly smaller than the systolic diameter 14b and systolic cross-sectional area 16b (FIG. 3B).

Figure 4A:
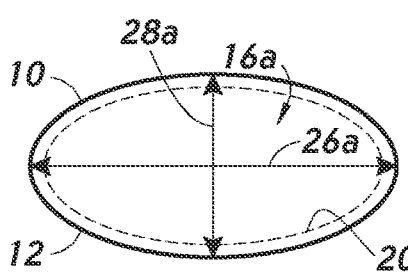
FIGS. 4A and 4B depict a compliant stent implanted within a blood vessel in accordance with one or more embodiments.
Figure 4B:
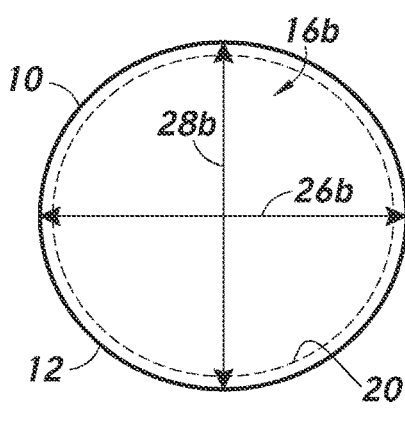

FIGS. 4A and 4B depict a compliant stent 20 implanted within a blood vessel 10. The stent 20 may be configured to restore compliance to the blood vessel 10. The stent 20 may comprise a stent wall configured to engage the blood vessel wall 12. In response to diastolic pressure, the stent 20 may be configured to have an oval diastolic shape with a major axis 26*a* and minor axis 28*a*. The stent 20 may be configured to cause the blood vessel 10 to assume a corresponding diastolic oval shape and/or diastolic cross-sectional area 16*a*. In response to systolic pressure, the stent 20 may be configured to assume a more circular systolic shape, which may cause the blood vessel wall 12 to assume a correspondingly more circular systolic shape where the stent minor axis 28*b* approaches or equals the stent major axis 26*b*, and/or with an enlarged systolic cross-sectional area 16*b*.

Figure 5A:
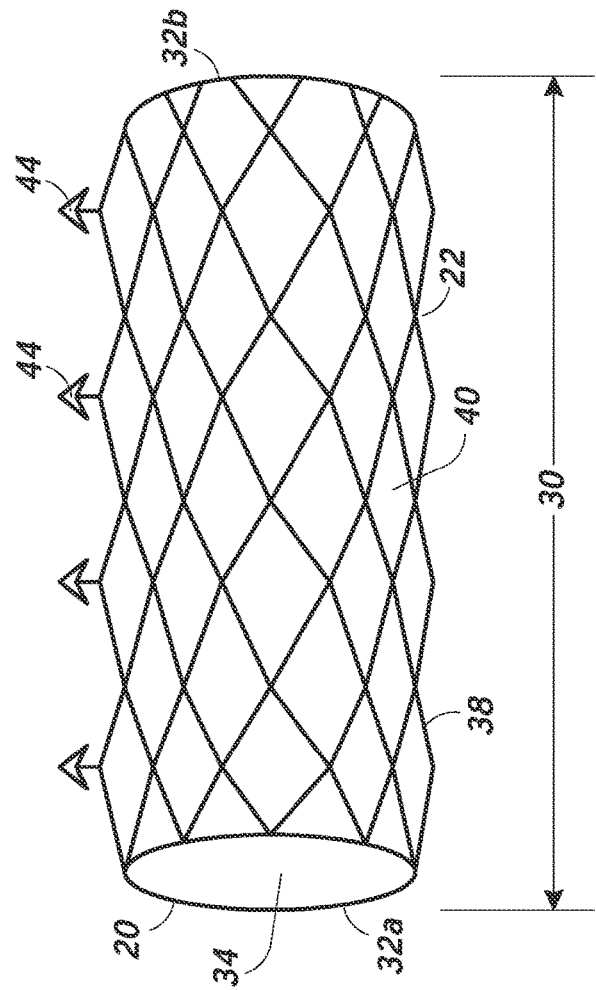
FIGS. 5A, 5B, and 5C depict views of a stent in accordance with one or more embodiments.
Figure 5C:
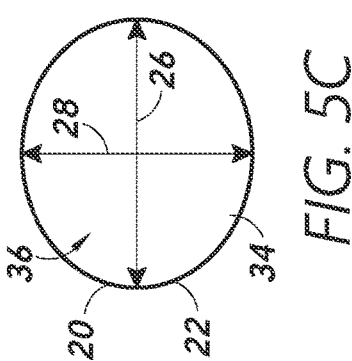
Figure 5B:
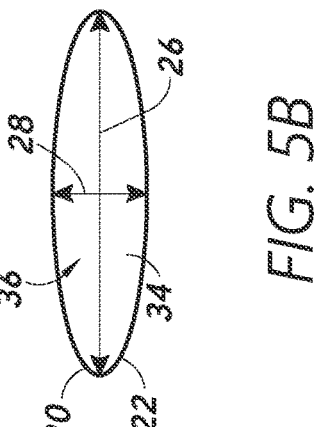

FIGS. 5A, 5B, and 5C depict views of a stent 20 according to some embodiments. The stent 20 may comprise a stent wall forming/defining an elongate/elongated tubular member. The stent and/or stent wall may comprise a first end 32*a* and/or second end, with a length 30 between a first end 32*a* and a second end 32*b* of the stent 20. The stent 20 may form a lumen 34 through a middle portion of the stent and/or passing from the first end 32*a* to the second end 32*b*, with a first opening at the first end 32*a* and/or a second opening at the second end 32*b*. In some embodiments, the stent 20 may be biased toward an oval (and/or other non-circular) cross-sectional shape lengthwise, where the stent lumen 34 may have a cross-sectional area 36 with a major axis 26 substantially larger than the minor axis 28. The stent 20 may be configured to increase compliance of a blood vessel though constant or near-constant pressure at a perimeter of the blood vessel to cause perimeter geometry change. For example, the blood vessel may be changed and/or moved from a non-circular shape and/or less circular shape to a circular and/or more circular shape.

The stent wall 22 may be at least partially composed of struts 38 and/or stent openings 40 between the struts 38. The dimensions and/or shape of the stent 20 may vary based on the particular application. The stent length 30 may be selected to extend over all or a portion of a non-compliant length of blood vessel. The stent major axis 26 and minor axis 28, when averaged, may be approximately equal to the diameter of the native blood vessel. For example, for a stent 20 configured for deployment in an aorta, the length 30 may be between 1 and 45 cm (or even longer if the entire length of the aorta is to be covered by the stent 20, and depending on the patient's anatomy), and in the biased oval/diastolic configuration the major axis 26 may be between 1.5 and 5 cm (or larger/smaller depending on the particular blood vessel parameters), and the minor axis 28 can be between 25 and 80 percent of the major axis 26. However, sizes and/or shapes are also within the scope of the disclosure.

The stent 20 may have an outer surface wall 22 with structures thereon to assist in securing the stent 20 to a blood vessel wall. For example, the outer wall 22 surface may be roughened and/or may have barbs 44 extending therefrom.

As shown in FIGS. 5B and 5C, the stent 20 may be biased toward an oval and/or other non-circular diastolic configuration, and may, when subjected to radially expansive forces, be configured to transform to a more circular systolic configuration where the minor axis 28 approaches and may equal the major axis 26.

The outer wall 22 of the stent 20 may be open or closed. For example, as shown in FIG. 5A, an "open" stent 20 may have one or more openings 40 in the outer stent wall 22 through which blood can freely pass. In some embodiments, the stent 20 may comprise an inner and/or outer lining and/or other layers which can prevent the flow of blood through the outer wall 22. A stent 20 comprising one or more openings 40 may be configured to cause the blood vessel wall to be loaded with a force resulting from the blood pressure (e.g., a tangential force) passing through the stent 20 as the heart beats. The blood pressure force on the blood vessel wall and resulting deflection thereof may permit deflection of the stent 20 to create a desired geometric change.

Figure 6C:
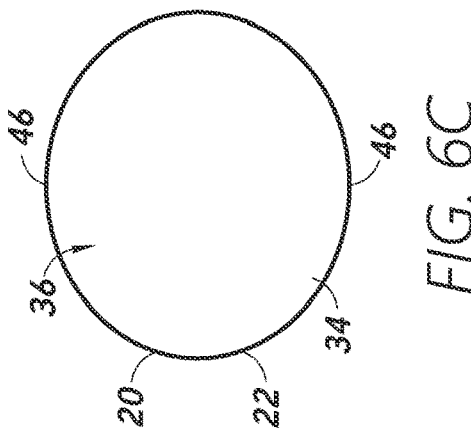
FIG. 6C depicts a stent deformed to a more circular shape in response to the larger pressures of systole according to one or more embodiments.
Figure 6B:
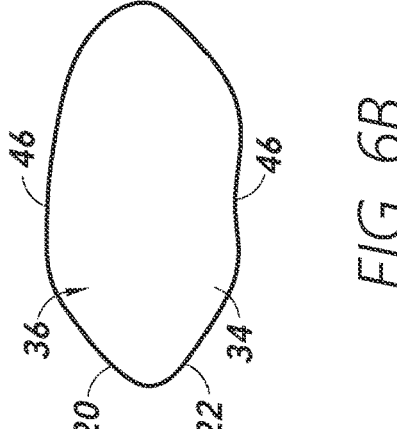
FIG. 6B depicts a stent deployed in a blood vessel and deformed into a substantially oval shape according to one or more embodiments.
Figure 6A:
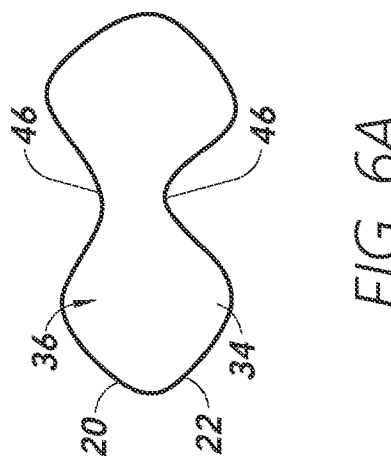
FIG. 6A depicts a stent that may be biased toward a "peanut" shape with mid-portions of the stent wall positioned inward such that the mid-portions may be relatively close together across the stent lumen.

Stents according to the invention may be biased toward various non-circular diastolic shapes. For example, FIG. 6A depicts a stent 20 that may be biased (such as being memory-set via a memory material such as Nitinol) toward a "peanut" shape with mid-portions 46 of the stent wall 22 positioned inward such that the mid-portions may be relatively close together across the stent lumen 34. Once deployed within a blood vessel, the stent 20 and blood vessel during diastolic pressure may remain in a somewhat peanut shape or, due to outward pressure from the blood within the blood vessel (even during diastole), the stent 20 and/or blood vessel may deform into a substantially oval shape as shown in FIG. 6B. When subjected to the larger pressures of systole, the stent 20 and/or blood vessel may deform to a more circular shape such as depicted above in FIG. 6C. In some embodiments, the stent 20 may be adapted to be secured firmly to the blood vessel wall (e.g., via barbs and/or endothelialization) so that the mid-portions 46 of the stent 20 may be configured to pull the blood vessel wall inwardly when the stent 20 deforms to its biased peanut (FIG. 6A) and/or oval (FIG. 6B) shape.

Figure 7B:
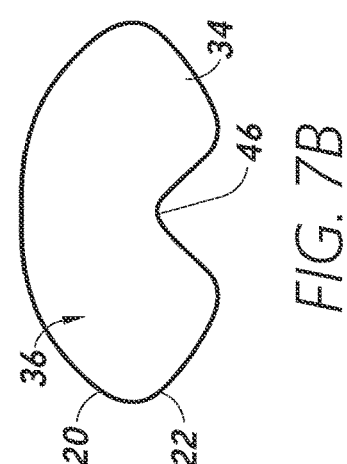
FIG. 7B depicts a stent biased toward a kidney shape according to one or more embodiments.
Figure 7A:
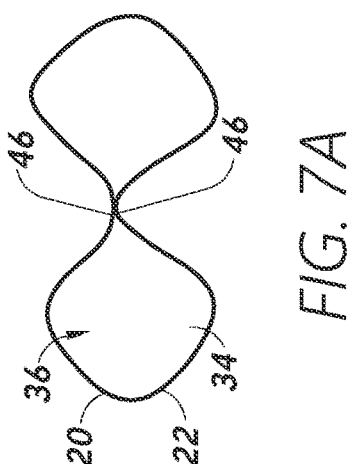
FIG. 7A depicts a stent biased toward a figure-8 shape according to one or more embodiments.

As depicted in FIG. 7A, a stent 20 may be biased toward a figure-8 shape, where the mid-portions 46 may be configured to touch each other across the stent lumen 34. The stent 20 may be configured to deform the blood vessel into a generally figure-8 shape during diastole and/or, due to due to outward pressure from the blood within the blood vessel (even during diastole), into a peanut or an oval shape or more circular shape. As depicted in FIG. 7B, a stent 20 may be biased toward a kidney shape where one mid-portion 46 may be distorted toward the center of the lumen 34. The stent 20 may be configured to distort the blood vessel during diastole into a kidney shape. During systole, the stent 20 and/or blood vessels may be configured to deform responsive to systolic pressure to press the central portion(s) 46 outward such that the stent/blood vessel may assume a larger cross-sectional area configuration, such as an oval, circular or more circular geometric cross-sectional shape. In some embodiments, the stent 20 may be adapted to be secured firmly to the blood vessel wall (e.g., via barbs and/or endothelialization) so that the mid-portions 46 of the stent 20 may pull the blood vessel wall inwardly when the stent 20 deforms to the biased figure-8, triangle, peanut, oval and/or kidney shape.

Stents 20 may be formed of various materials, such as Nitinol and/or other shape-memory materials. In some embodiments, stents 20 may be laser-cut from a tube, formed from wire-form, and/or shaped into a desired stent form. A stent 20 and/or other device may be configured to improve blood vessel compliance. In some embodiments, a stent 20 may be configured to engage a blood vessel wall and/or reshape the blood vessel to a smaller cross-sectional area (e.g., a non-circular shape) during systole. The stent 20 may be configured to reshape the blood vessel during diastole to any desired shape, including a "peanut," "kidney," "racetrack," oval, triangle, and/or other shape. After the blood vessel is reshaped, the stent may be configured to expand the blood vessel to a larger cross-sectional area (e.g., a generally circular and/or more circular shape) during systole.

In some embodiments, portions of a stent 20 may be separated from other portions of the stent 20 and/or a stent 20 may be separated from other stents by cloth, polymer film, sutures, and/or other materials to improve abrasion.

In some embodiments, a stent 20 may have a spring constant ("k"). The spring constant may define a stiffness of the stent 20 and/or an ability/tendency of the stent 20 to resist deformation. Stents 20 configured for delivery into high pressure blood vessels (e.g., the aorta) may be config- ured to have a spring constant that is relatively high in order to be able to hold the blood vessel in the desired non-circular geometry. However, a stents 20 may be configured such that the spring constant is not so high that it prevents the stent 20 from deforming to permit the blood vessel to achieve the desired circular/more circular geometry during systole. To achieve such a spring response, a stent 20 may be con- structed using relatively thick wall tubing (e.g., for stents cut out of a tube) and/or using relatively large diameter wires (e.g., for stents formed from wire-forms and/or wire braids). In some embodiments, a stent 20 may be composed at least partially of Nitinol due to its super-elasticity.

The outer wall 22 of the stent 20 may be open or closed. For example, as shown in FIG. 5A, an "open" stent 20 may have one or more openings 40 in the outer stent wall 22 through which blood can freely pass. In some embodiments, the stent 20 may comprise an inner and/or outer lining and/or other layers which can prevent the flow of blood through the outer wall 22. A stent 20 comprising one or more openings 40 may be configured to cause the blood vessel wall to be loaded with a force resulting from the blood pressure (e.g., a tangential force) passing through the stent 20 as the heart beats. The blood pressure force on the blood vessel wall and resulting deflection thereof may permit deflection of the stent 20 to create a desired geometric change.

Figure 8B:
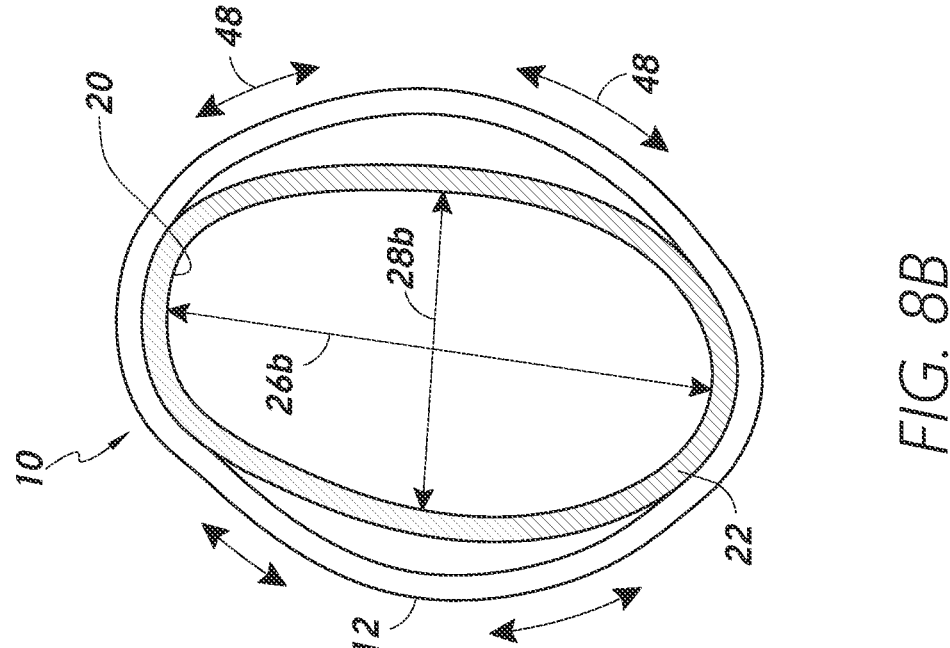
FIGS. 8A and 8B depict a blood vessel with a stent portion having an open stent wall through which blood can freely flow according to one or more embodiments.
Figure 8A:
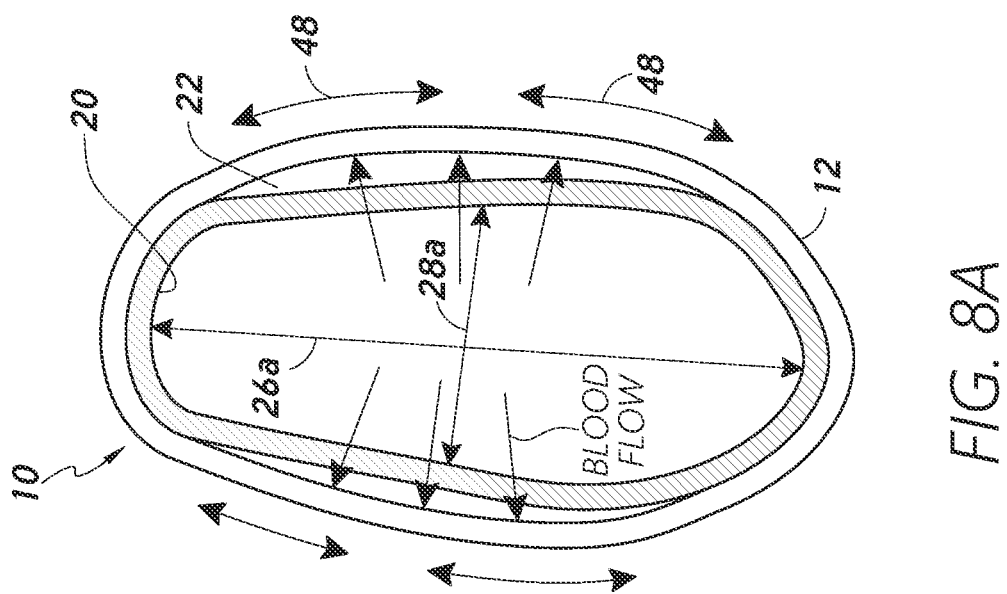

FIGS. 8A and 8B depict a blood vessel 10 with a stent 20 portion having an open stent wall 22 through which blood can freely flow. In FIG. 8A, the stent 20 portion may have a generally non-circular (e.g., oval) shape with a major axis 26a and minor axis 28a. As blood pressure increases in the blood vessel 10, the stent 20 may be configured to allow blood to pass through the open stent wall 22 and/or press against the blood vessel wall 12. The blood pressure may accordingly create tension 48 in the blood vessel wall 12, particularly in the blood vessel wall portions running roughly parallel to the stent major axis 26a. The tension 48 may result in the blood vessel 10 compressing the stent 20 along the major axis 26a of the stent 20, causing the stent 20 to assume a less oval/more circular shape as depicted in FIG. 8B, where the major axis 26b may be shorter than it was prior to the increase of blood pressure (shown in FIG. 8A) and/or the blood vessel 10 may have a larger cross-sectional area than in the more oval shape of FIG. 8A.

For a closed/covered stent 20, blood may be prevented from flowing through the stent 20 to press outwardly against the blood vessel wall 12. Instead, pressure load may act directly onto the stent 20 via a lining material of the stent 20 (e.g., polymer film, bio-prosthetic material, cloth, etc.). For such closed/covered/lined stents 20, one or more materials of the stent 20 may create a sealing between the stent 20 and the blood vessel wall 12 and/or between the stent 20 and one or more adjacent stents 20 which may be deployed in the same blood vessel 10. Such sealing can be achieved using deflections in the outer surface of the stent 20, such as in the form of raised and/or lowered features in the outer surface of the stent 20. Examples of such features can include raised and/or lowered features (e.g., raised bumps or edges or lowered troughs) at the distal and/or proximal ends of the stent 20 for improved sealing at the leading and/or trailing stent edges and/or against the native anatomy. Raised and/or lowered features such as bumps and/or ridges and/or troughs may be configured to be positioned at various positions along the length of the stent 20. Raised and/or lowered features may be formed in various ways, for example using compliant materials such as cloth, foam, elastomers, etc.

Figures 9, 10:
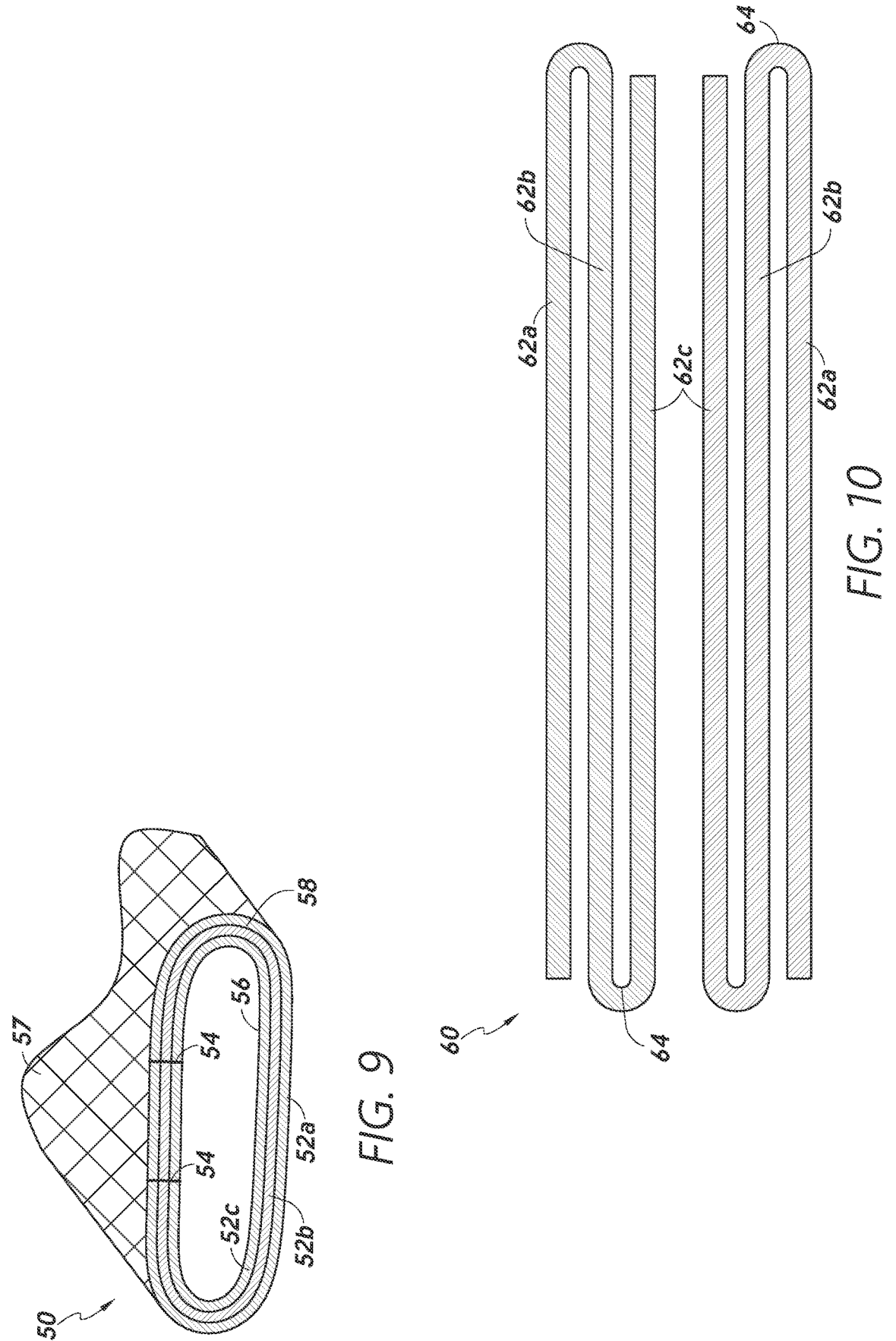
FIG. 9 depicts a device formed using multiple layers of stent portions stacked together in a tube-within-a-tube configuration according to one or more embodiments disclosed herein.
FIG. 10 depicts a multi-layered stent construction in accordance with one or more embodiments.

FIG. 9 depicts a device 50 formed using multiple layers of stent portions 52a, 52b, 52c stacked together in a tube-within-a-tube configuration. The device 50 may utilize a multiple-stent-layer configuration that can provide an over-all spring response for the device 50 which can be sufficient to provide desired geometrical shape changes responsive to blood pressure changes. In some embodiments, one or more of the stent portions 52a, 52b, 52c may comprise laser-cut stent portions, wire-form stent portions, braided stent por-tions, other stent portions, and/or any combination of laser-cut, wire-form, braided, and/or other stent portions. The stent portions 52a, 52b, 52c may be configured to be interconnected using connections 54, which may include polymer films, cloths, suture, and/or wire. The device 50 may comprise additional layers, such as an inner lining layer 56, outer lining layer 57, and/or layers 58 which may be configured to separate the stent portions 52a, 52b, 52c. Such layers may be at least partially composed of cloth, polymer film, suture, and/or other materials.

In some embodiments, each stent portion 52a, 52b, 52c may be of similar construction to the other portions. How-ever, different stent portions 52a, 52b, 52c can have differing constructions. For example, a first stent portion 52a may comprise a tube-cut stent and a second stent portion 52b may comprise a wire-form stent. All or some stent portions 52a, 52b, 52c may be preassembled ahead of the stent deploy-ment, so that the stent portions may be delivered as part of a single pre-assembled device 50. All or some stent portions 52a, 52b, 52c may be configured to be delivered serially into the patient and/or assembled on site. In such embodiments, some such stent portions 52a, 52b, 52c may comprise radiopaque markers for improved viewing by a surgeon or other user of the stent-to-stent alignment. Some stent por-tions 52a, 52b, 52c may comprise magnetic elements for improved stent-to-stent alignment and engagement. Various other stent-to-stent engagement features may be used, such as Velcro attachments, etc.

FIG. 10 depicts a multi-layered stent 60 construction. In some embodiments, a multi-layered stent 60 may be formed by folding and/or inverting a stent 60 within/onto itself one or more times to provide multiple stent layers 62a, 62b, 62c. Adjacent layers 62a, 62b, 62c may be joined by folds 64. The device 60 may include other layers and connections, such as an outer lining, separating layers, and/or connections (see, e.g., FIG. 9). Folding of the stent 60 or stents 60 may be performed prior to delivery and/or may be performed inside the patient, such as within the targeted blood vessel.

Figure 11:
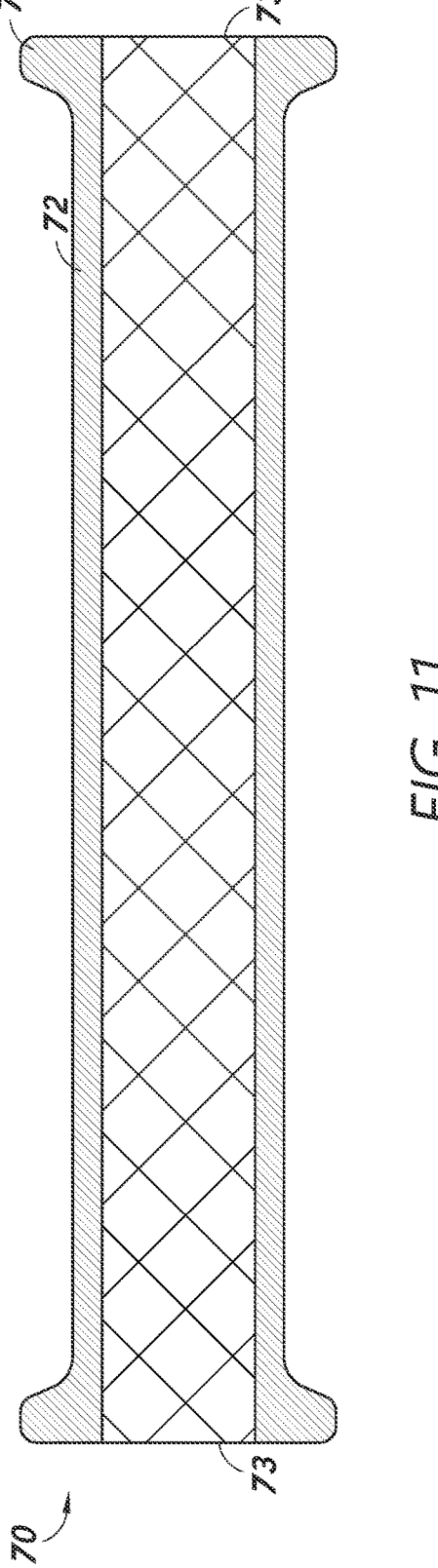
FIG. 11 depicts a stent having one or more raised edges at an outer wall of the stent which can provide improved sealing against the vessel walls of a blood vessel in which the stent may be implanted in accordance with one or more embodiments.

FIG. 11 depicts a stent 70 having one or more raised edges 71 at an outer wall 72 of the stent 70 which can provide improved sealing against the vessel walls of a blood vessel in which the stent 70 may be implanted. In some embodi-ments, the raised edges 71 may be positioned at the ends 73 of the device 70, and/or at other positions along the length of the device 70. The edges 71 may be in addition to the hooks and/or rough surfaces configured for securing the stent 70 to the blood vessel wall.

Figure 12:
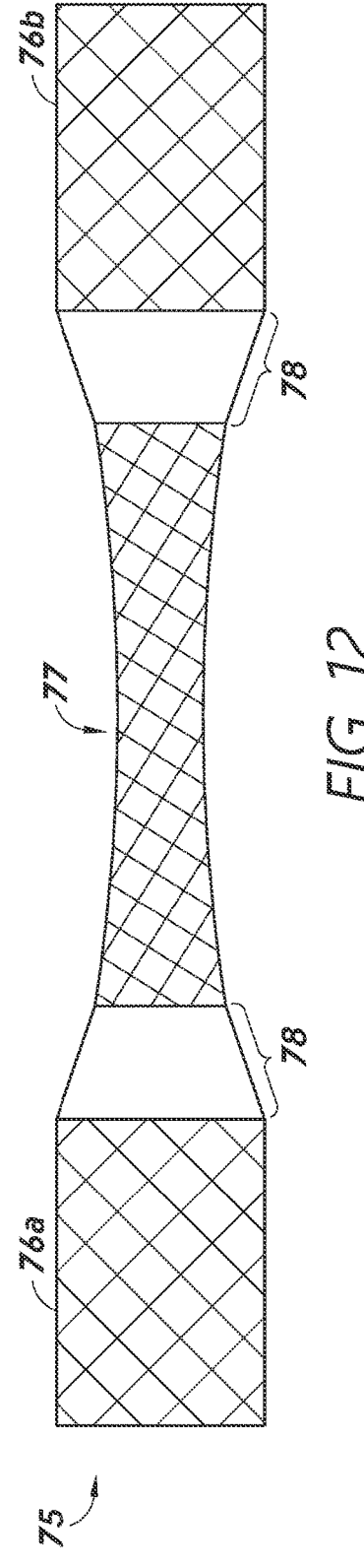
FIG. 12 depicts a stent assembly configured to create sealing in accordance with one or more embodiments.

FIG. 12 depicts a stent assembly 75 configured to create sealing, which can be achieved using a hybrid material. For example, a stent assembly 75 may comprise balloon-ex-pandable stent portions at the end portions 76 (e.g., distal end portion 76b and/or proximal end portion 76a) of the stent assembly 75, with a self-expanding stent portion mak-ing up the middle portion 77 of the stent assembly 75. In some embodiments, the end portions 76 may be at least partially formed from plastically deformable/balloon expandable materials, such as stainless steel and/or cobalt alloys (e.g., cobalt chromium). The middle portion 77 may be at least partially composed of a shape-memory material (e.g., Nitinol). In some embodiments, the end portions 76 may be configured to be secured to the middle portion 77 via various direct and/or indirect connections. For example, connections may include suture, wire, film, cloth, etc. Connections may be configured to form transition sections 78 extending between the middle portion 77 and respective end portions 76. In some embodiments, balloon-expandable components may be configured to facilitate embedding attachment features (e.g., barbs and/or hooks) of the stent assembly 75 to tissue and/or for other sealing purposes. The end portions 76 and/or middle portion 77 may be configured to surround lumens configured to allow blood to flow through the stent assembly 75 and/or to contact a blood vessel wall that the stent assembly 75 may be configured to secure to.

Figure 13B:
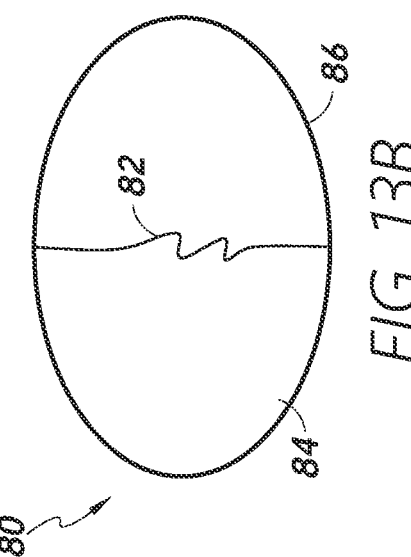
FIGS. 13A and 13B depict a stent comprising springs which may extend across a stent lumen and/or may be configured to cause the stent to deform in accordance with one or more embodiments.
Figure 13A:
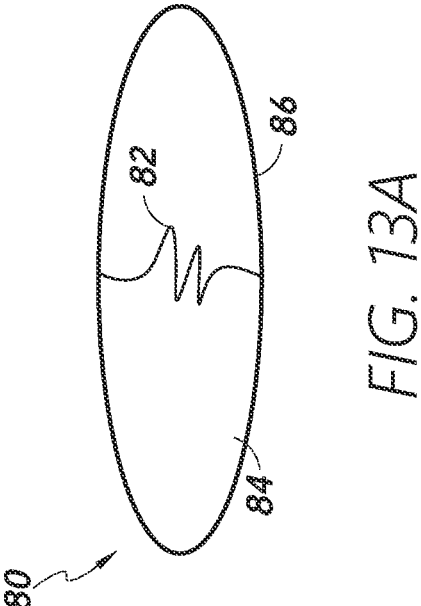

FIGS. 13A and 13B depict a stent 80 comprising springs which may extend across a stent lumen 84 and/or may be configured to cause the stent 80 to deform. For example, the stent 80 may comprise a spring 82 (e.g., a coil spring) configured to extend across the stent lumen 84. In response to diastolic pressure, the spring 82 may be configured to pull the outer wall 86 of the device 80 toward a desired biased form, such as the depicted oval shape shown and/or another shape, e.g., triangle, peanut, figure-8, etc. However, systolic pressure may be sufficient to at least partially overcome the force of the spring 82 and/or to expand the stent 80 to a larger-cross-sectional area shape, such as the more circular shape depicted in FIG. 13B.

Figure 14B:
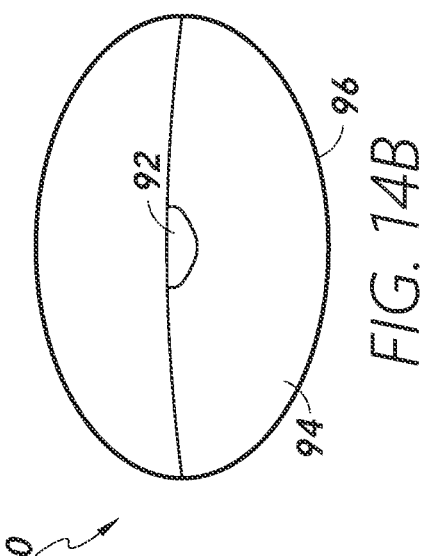
FIGS. 14A and 14B depict a stent comprising a spring configured to extend across a stent lumen in accordance with one or more embodiments.
Figure 14A:
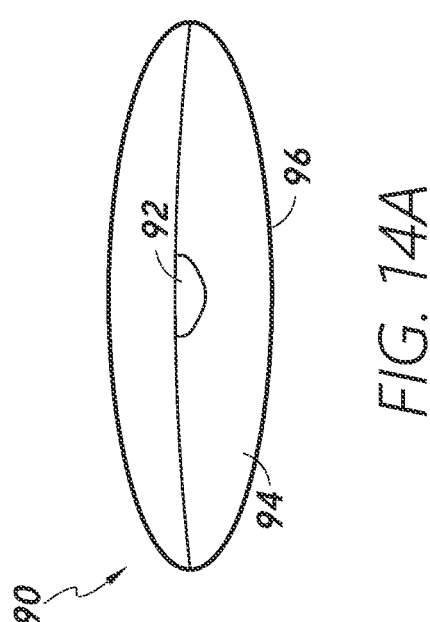

FIGS. 14A and 14B depict a stent 90 comprising a spring 92 (e.g., a torsion spring) configured to extend across a stent lumen 94. The spring 92 may be configured to push against a wall 96 of the stent 90 to bias the stent 90 toward a desired form, such as the oval shape depicted in FIG. 14A and/or another shape, e.g., triangle, peanut, etc. During systole, the blood pressure may be sufficient to at least partially overcome the spring 92 and/or to expand the stent 90 to a larger cross-sectional area shape, such as the more circular shape depicted in FIG. 14B.

Figures 15A, 15B:
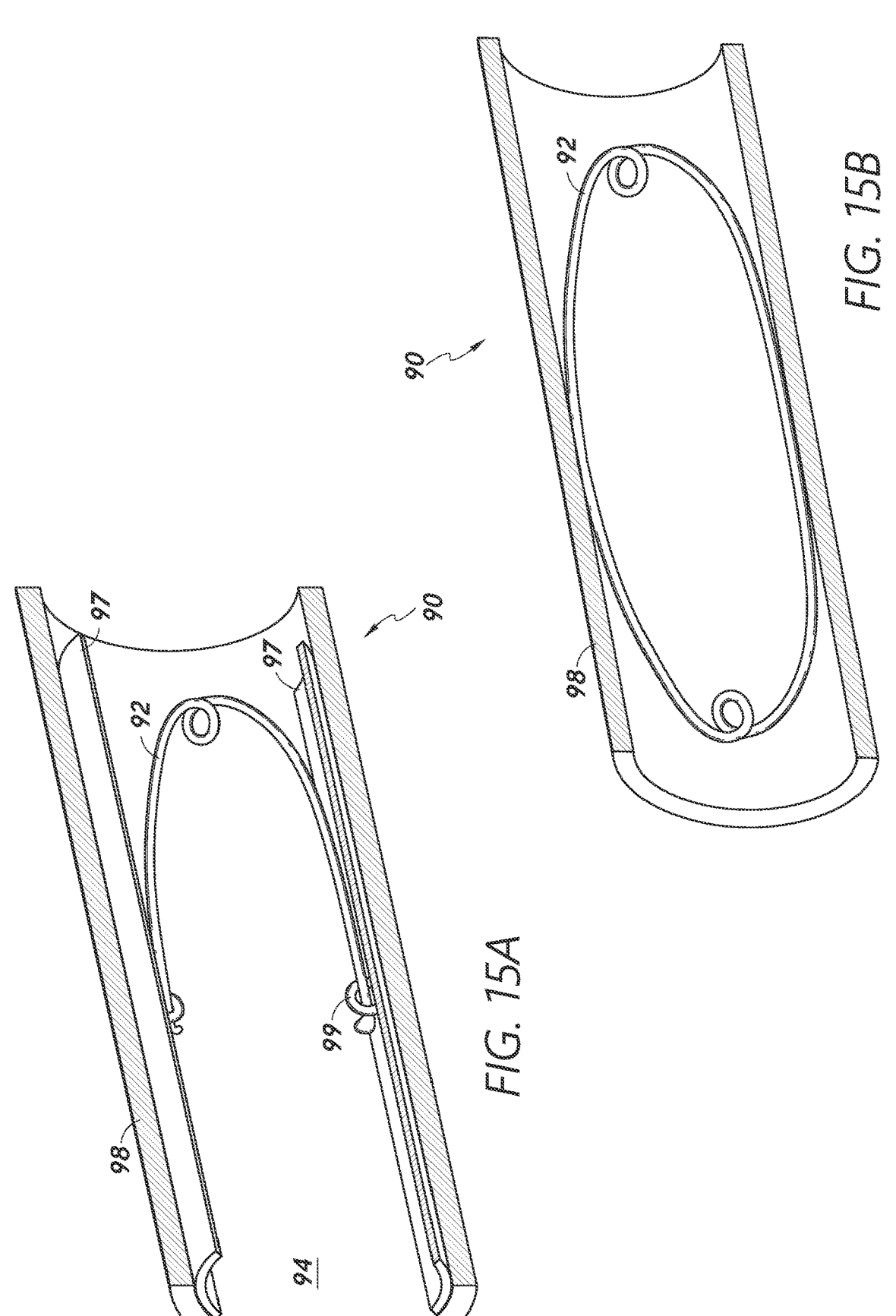
FIGS. 15A and 15B depict another stent comprising a spring in accordance with one or more embodiments.
Figure 15C:
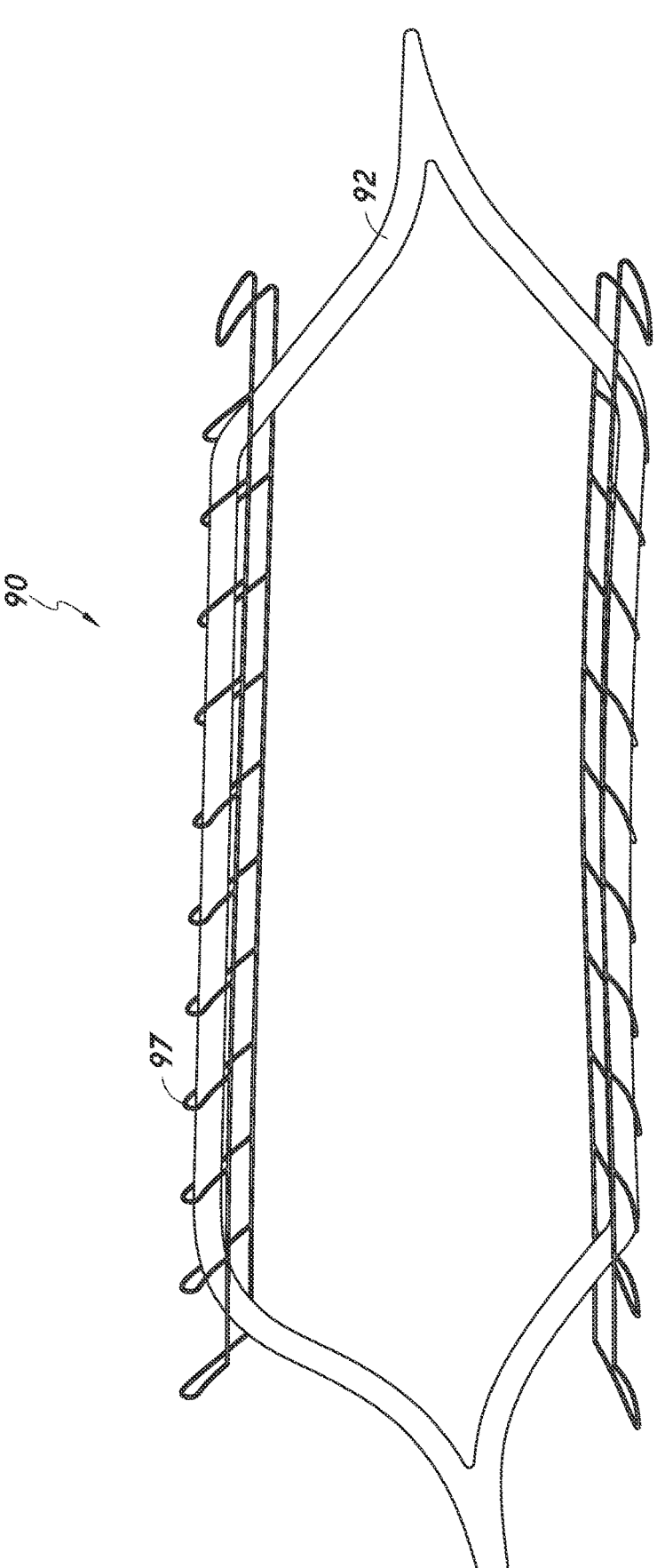
FIG. 15C depicts a stent comprising a single torsion spring in accordance with one or more embodiments.

FIGS. 15A and 15B depict another stent 90 comprising a spring 92. The stent may be open (i.e., may allow blood flow through the stent 90). In some embodiments, the stent 90 may comprise pad structures 97 which may be configured to protect a blood vessel wall 98 from spring structures such as spring ends 99. The spring 92 may be configured to press outwardly against the blood vessel wall 98 to create the desired oval and/or less circular shape when blood pressure is low, but during higher blood pressure the blood vessel may press back against the spring 92 with greater strength and thereby may assume a more circular and/or less oval shape having a larger cross-sectional area. FIG. 15C depicts a stent 90 comprising a single torsion (i.e., "wishbone") spring 92. The torsion spring 92 may be formed from wire, cut from a tube, cut from sheet metal, formed from non-metal materials, etc.

While in some embodiments, a stent may comprise a single length of linear tube, stents may comprise multiple lengths of linear tube and/or other forms. For example, a stent may comprise Y-shaped structures wherein a stent with a bifurcated end may be provided to fit an anatomical bifurcation. In such an embodiment, various portions of the Y-shape may be biased toward the same general shape and/or may be biased toward different shapes. For example, a main base/leg of the Y-shape structure may be biased toward a first shape (e.g., oval shape), a left upper arm portion of the Y-shape may be biased toward a second shape (e.g., kidney shape), and/or a right upper arm portion of the Y-shape may be biased toward a third shape (e.g., circular shape). Any combination of the shapes disclosed herein can be applied to the various portions of a device of the various embodiments described herein.

Figure 16B:
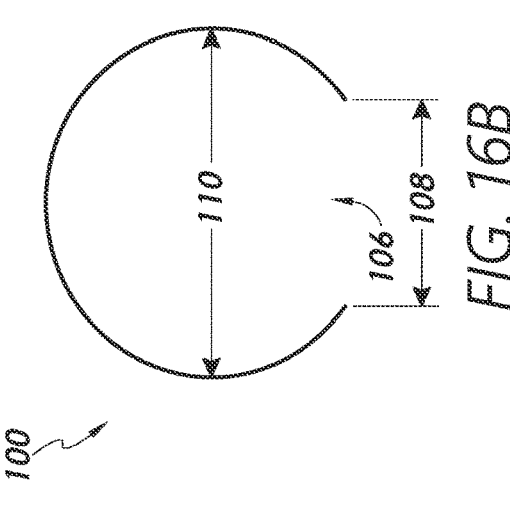
FIGS. 16A and 16B depict a stent adapted to be secured around a blood vessel in accordance with one or more embodiments.
Figure 16D:
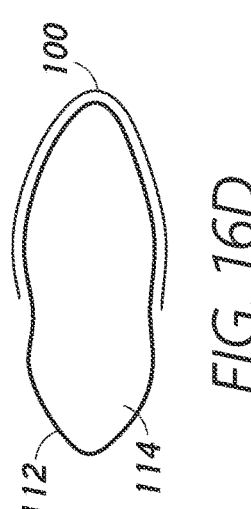
FIG. 16D depicts the stent during systole in accordance with one or more embodiments.
Figure 16A:
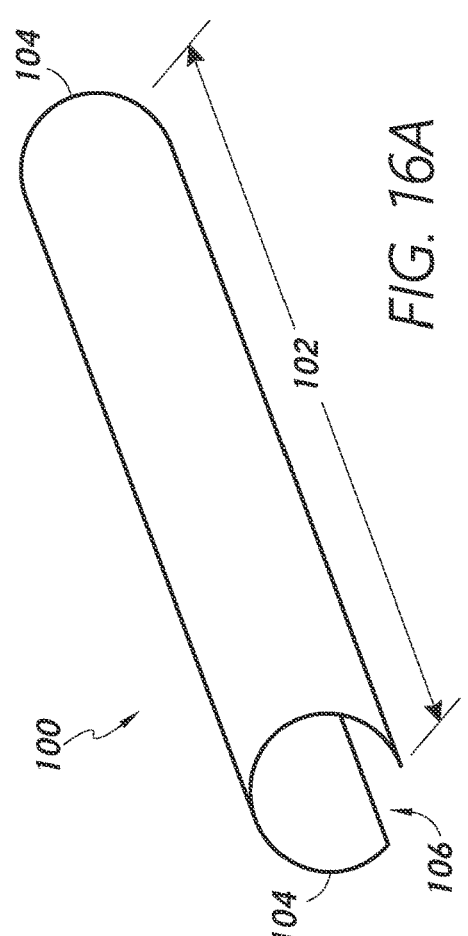

FIGS. 16A and 16B depict a stent 100 according to an embodiment of the invention adapted to be secured around a blood vessel. The stent 100 may be generally C-shaped in cross-section (see, e.g., FIG. 16B), with a length 102 and opposing ends 104. The stent 100 may comprise a side opening 106 having an opening width 108 adapted to slidingly receive a length of blood vessel therein in order to secure the stent 100 around the length of blood vessel. The stent 100 may have inner dimensions such as an inner diameter 110 adapted to receive at least a portion of a cross-sectional area of the blood vessel therein.

Figure 16C:
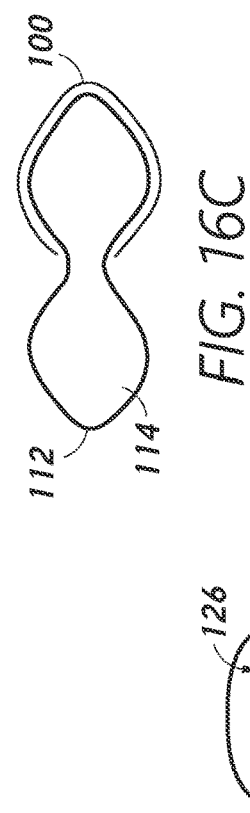
FIG. 16C depicts the stent during diastole in accordance with one or more embodiments.

FIG. 16C depicts the stent 100 during diastole, wherein the stent 100 may be configured to hold a blood vessel 112 with the lumen 114 in a smaller cross-sectional area shape (e.g., the generally peanut shape depicted). FIG. 16D depicts the stent 100 during systole, in which the blood vessel 112 may expand to a larger cross-sectional area shape having an enlarged lumen 114, such as the generally oval shape depicted.

In some embodiments, stents may comprise various features to assist in deployment and/or operation of the stents. For example, a stent may comprise one or more radiopaque markers at various locations along a length of the stent. Moreover, a stent may comprise one or more active features, such as electrical features (e.g., pressure, temperature, strain, and/or accelerometer sensors).

Figure 17:
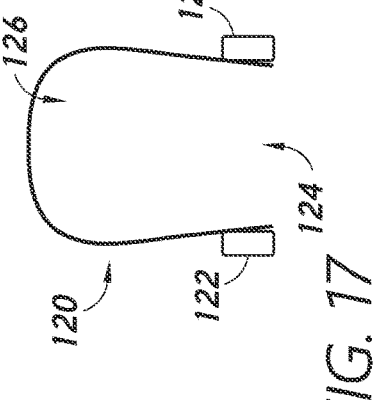
FIG. 17 depicts a stent comprising one or magnets which may be configured to pull and/or push portions of the stent together/apart in order to provide desired geometric modifications of a blood vessel in accordance with one or more embodiments.

FIG. 17 depicts a stent 120 comprising one or magnets 122 which may be configured to pull and/or push portions of the stent 120 together/apart in order to provide desired geometric modifications of a blood vessel. Such magnets 122 may be configured to pull and/or push against other magnets 122 of the stent 120 and/or other stents. In some embodiments, the magnets 122 may be situated on either side of a side opening 124 leading to a lumen 126 of the stent 120. The magnets 122 may be configured to be positioned at various positions along the length of the stent 120.

Figure 18B:
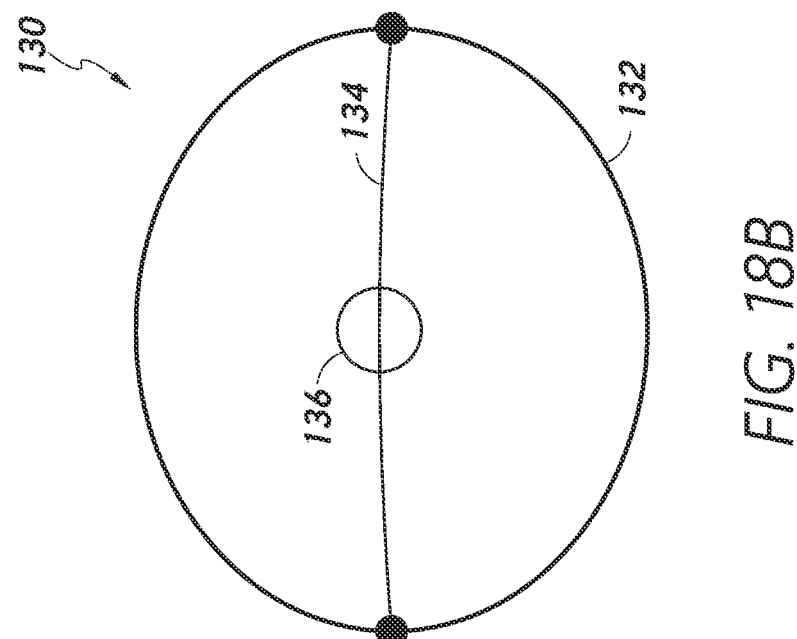
FIG. 18B depicts a stent held in a generally circular, more circular, and/or less oval shape in accordance with one or more embodiments.
Figure 18A:
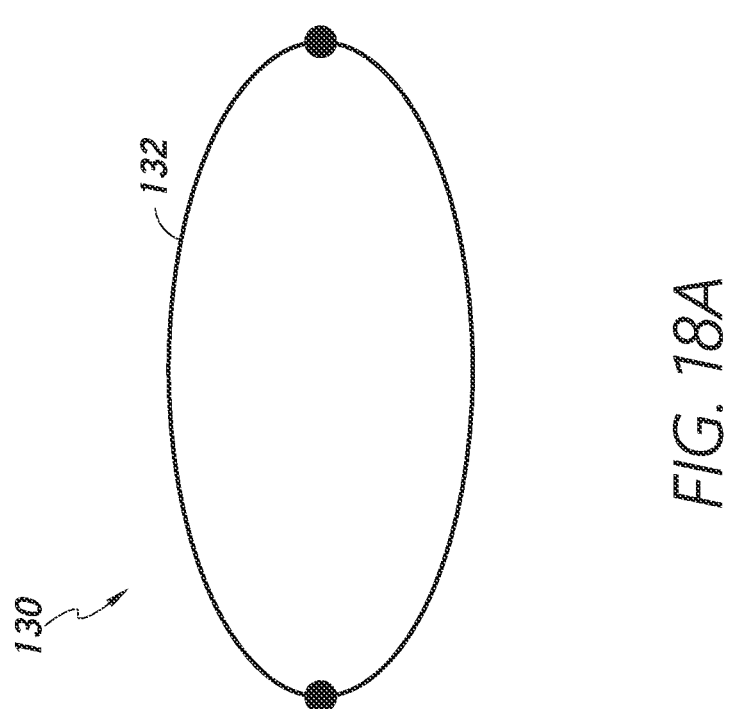
FIG. 18A depicts a stent biased toward an oval and/or other non-circular shape in accordance with one or more embodiments.

FIG. 18A depicts a stent 130 biased toward an oval and/or other non-circular shape, while FIG. 18B depicts the stent 130 held in a generally circular, more circular, and/or less oval shape. In some embodiments, holding the stent 130 in the more circular shape of FIG. 18B may enable tissue of a blood vessel (not shown) to overgrow into the stent wall 132. When the blood vessel is secured to the stent wall 132 via tissue overgrowth/ingrowth, the stent 130 can be released to assume a more oval and/or less circular shape, which can thereby cause the blood vessel to assume a more oval and/or less circular shape. In some embodiments, the stent 130 may comprise a tension element 134 (e.g., a wire, suture (e.g., dissolvable suture), cloth, etc.) configured to extend across the stent 130 and holds it in the more circular shape. After the stent 130 is deployed in the blood vessel and the tissue has overgrown/ingrown to the stent wall 132, the tension element 134 (e.g., wire, suture, cloth, etc.) can be removed, such as by cutting and/or removal by a surgeon or other user. In some embodiments, the tension element 134 may be at least partially composed of a material configured to dissolve over time. For example, the tension element 134 may be configured to at least partially dissolve over time due at least in part to contact with blood and/or other bodily fluids and/or tissues. In some embodiments, the tension element 134 may comprise and/or may be configured to be secured to a coupling device 136 adapted to interact with a catheter (not shown) which can be advanced through one or more body lumens of the patient (e.g., via the patient's vasculature) and coupled with the coupling device 136 in order to effectuate cutting and/or removal of the tension element 134.

Figure 19A:
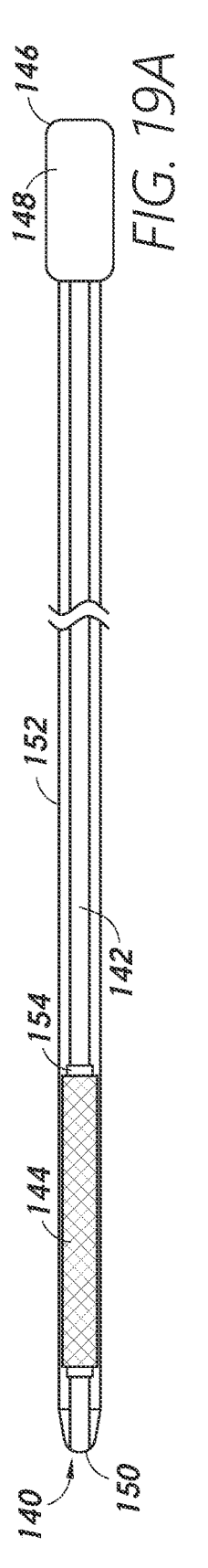
FIG. 19A depicts an example of a system with a delivery catheter for deploying a stent in accordance with one or more embodiments.

FIG. 19A depicts an example of a system 140 with a delivery catheter 142 for deploying a stent 144. The delivery catheter 142 may comprise a proximal end 146 with a handle 148 with controls thereon. The delivery catheter 142 may further comprise a distal end 150 adapted to be advanced into a blood vessel, such as via percutaneous methods. The system 140 may further comprise a retractable sheath 152 configured to cover and/or protect the stent 144 during delivery. In some embodiments, the sheath 152 may be configured to be retracted to permit the stent 144 to expand at a desired deployment position. The catheter 142 may comprise an expandable balloon 154 which can be selectively expanded in order to expand the stent 144 firmly into contact with a blood vessel wall. For a self-expanding stent, the balloon 154 can add further expansion to firmly engage the stent 144 against a blood vessel wall. In some embodiments, components of the system 140 may be configured to be loaded onto the delivery catheter 142 via various methods. For example, radial crimping, folding, and/or rolling may be used to load onto the catheter 142.

Figure 19B:
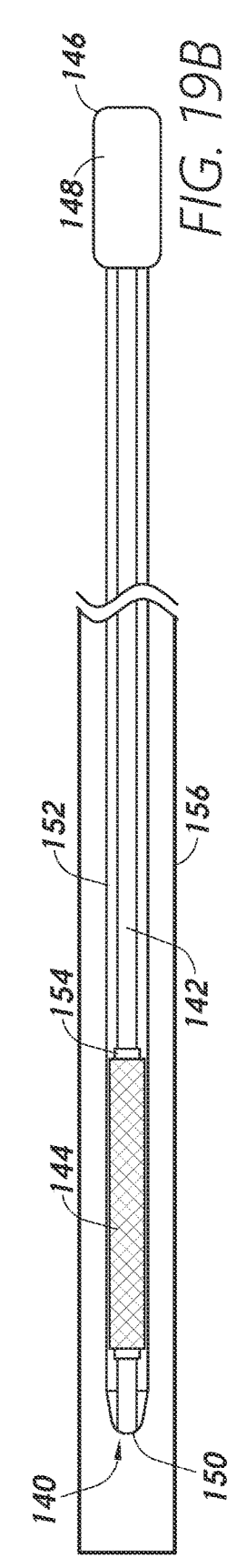
FIGS. 19B, 19C, and 19D depict side views of deployment of the stent within a blood vessel using the delivery catheter in accordance with one or more embodiments.
Figure 19C:
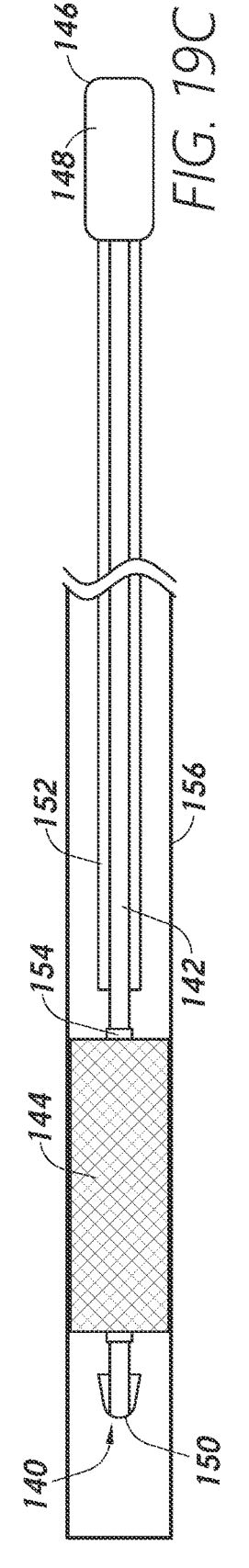
Figure 19D:
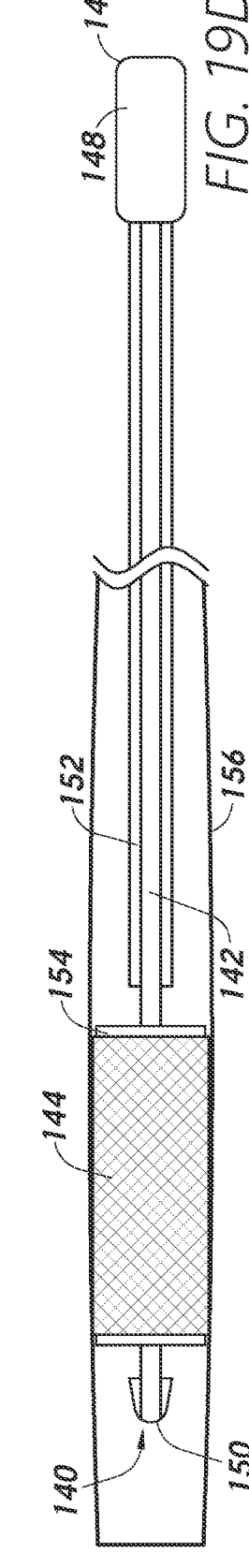

FIGS. 19B, 19C, and 19D depict side views of deployment of the stent 144 within a blood vessel 156 using the delivery catheter 142. The distal end 150 of the delivery catheter 142 may be advanced into the blood vessel 156 to a desired deployment location, as depicted in FIG. 19B. The sheath 152 may be retracted, at which point a self-expanding stent 144 may be configured to radially expand, as shown in FIG. 19C. The balloon 154 may be expanded to expand the stent 144 and/or to over-expand a self-expanding stent 144 to firmly press the stent 144 against the wall of the blood vessel 156, as depicted in FIG. 19D. After the stent 144 is properly deployed, the catheter 142 can be withdrawn from the patient. The sheath 152 may be advanced to a closed position (e.g., back over the balloon 154) prior to withdrawal of the catheter 142. With the stent 144 deployed in the blood vessel 156, the stent 144 may be configured to deform the blood vessel 156 as desired during diastole and/or systole to vary the blood vessel cross-sectional area responsive to heart beats of the patient in order to restore some blood vessel compliance.

Various approaches for treatments, including advancing the catheter 142 into position via the sheath 152, are within the scope of this disclosure. In some embodiments, artery access may be obtained via an access sheath 152 dimensioned for use in some procedures. An incision may be created in a patient, leading to an internal blood vessel 156 (e.g., a femoral artery). The distal end of the access sheath 152 may be advanced through the incision and internal blood and into a desired position within the target blood vessel 156, with the catheter handle 148 positioned outside the patient adjacent the incision/access site. Echo and/or fluoroscopic and/or other visualization techniques may be used to confirm proper position of the stent 144. The treatment and/or implant deployment can occur, such as by deploying the stent 144 at the target location. Once the proper deployment is confirmed, the catheter 142 can be removed from the patient, and the incision(s) may be closed, for example via sutures.

Migration of stents and/or other devices according to the invention can be prevented using various methods, elements, and combinations thereof. For example, endothelialization of the stent wall and/or projecting barbs can be used to secure devices to the blood vessel wall. In addition to such elements/techniques and/or in lieu of such elements/techniques, devices of the invention may include anchors adapted to extend into branching blood vessels/structures, which can serve to anchor the device in the main blood vessel in which the main stent body is deployed. For example, a device may comprise a main stent body (such as any of the stent assemblies discussed previously in this application) adapted to be deployed in a main blood vessel to provide compliance thereto, such as where the main stent body is adapted to change from a smaller cross-sectional area to a larger cross-sectional area. The device may further have one or more anchors extending in a non-parallel fashion from the main stent body. The particular anchors may each comprise an anchor stent body adapted to be deployed (such as via radial expansion) into contact with tissue (e.g., wall tissue) of a secondary blood vessel or other vascular structure which can branch off and/or otherwise extend generally sideways from the main blood vessel. Note that multiple anchors and/or stents may be used and/or can extend from different locations along the length and/or radial perimeter of the main stent body, depending on the particular application. One or more anchors may preferably be positioned at locations which can align with secondary blood vessels/structures as they branch off/extend from the main blood vessel. In some embodiments, the anchors may be self-expanding or plastically deformable (such as via balloon expansion). The anchors may, once expanded or otherwise deployed into contact with the tissue of the secondary blood vessel/structure, form generally circular lumens, oval lumens, peanut-shaped lumens, etc., and/or may be adapted to maintain a generally constant cross-sectional area and/or may be adapted to change from smaller cross-sectional area to larger cross-sectional area configurations responsive to blood flow.

Figure 20A:
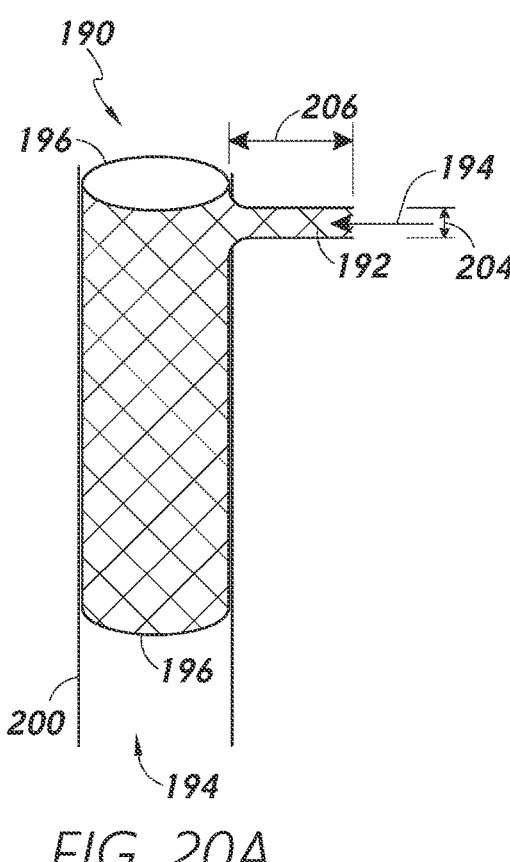
FIG. 20A depicts a stent comprising an anchor portion configured to be positioned along and extending from a main stent body between ends of the stent in accordance with one or more embodiments.

FIG. 20A depicts a stent 190 comprising an anchor portion 192 configured to be positioned along and extending from a main stent body 194 between ends 196 of the stent 190. The anchor portion 192 may be configured to be deployed in a side blood vessel branching and/or extending from a main blood vessel 200. For example, the anchor portion 192 may be configured to be situated at least partially in a renal artery while the main stent body 194 may be configured to be situated at least partially in an abdominal aorta). The anchor portion 192 may have an expanded diameter 204 which may be sufficient for the walls of the anchor portion 192 to engage the respective blood vessel wall (e.g., the expanded diameter 204 may be approximately 4 to 7 mm for delivery in the renal arteries). The anchor portion 192 may preferably have a length 206 which may be sufficient for the anchor portion 192 to be firmly secured within the side blood vessel (e.g., renal artery) while resisting displacement which might otherwise be caused by dynamic forces acting on the anchor portion 192 and/or on the main stent body 194 from which the anchor portion 192 may extend. For example, the length may be in the range from 0.5 to 7 cm for delivery in the renal arteries. In some embodiments, the stent 190 may comprise two or more anchor portions 192 extending from the main stent body 194 at positions between the main body stent ends 196, and/or each of the anchor portions 192 may be configured to extend at least partially into a branch and/or extension of a main blood vessel 200.

Figure 20B:
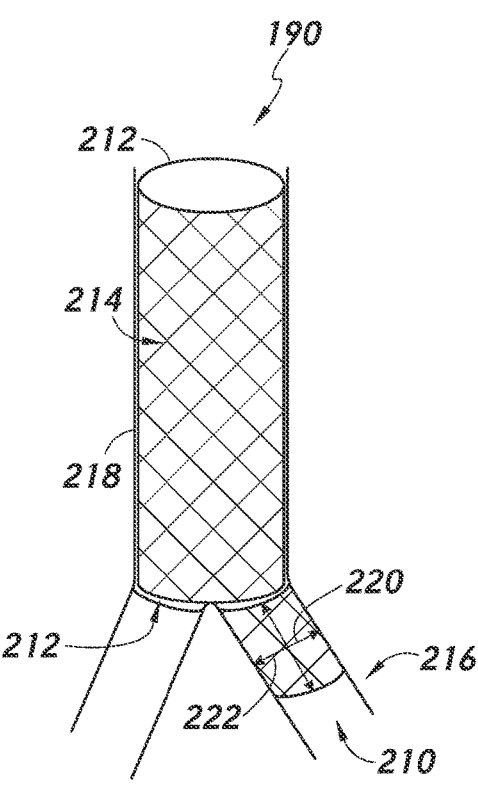
FIG. 20B depicts a stent comprising an anchor portion configured to extends from an end portion of a main stent body in accordance with one or more embodiments.

FIG. 20B depicts a stent 190 comprising an anchor portion 210 configured to extends from an end portion 212 of a main stent body 214. In some embodiments, the anchor portion 210 may be configured to be deployed within a branch blood vessel 216 which branches (e.g., via bifurcation) from a main blood vessel 218. For example, the main stent body 214 may be configured to be deployed in the abdominal aorta and/or the anchor portion 210 may be configured to be deployed within an iliac artery adjacent the aortic bifurcation. In some embodiments, the anchor portion 210 may have an expanded diameter 220 which may be configured to approximate a diameter of the branch blood vessel 216 (e.g., the iliac artery) and/or a length 222 sufficient to secure the anchor within the branch blood vessel 216. The anchor portion 210 may be in the form of a stent and/or may form a lumen having any suitable shape, for example a circular, oval, peanut, and/or other shape. In some embodiments, the anchor portion 210 may be configured to be biased toward a first configuration wherein the lumen may have a smaller cross-sectional area than in a second configuration (e.g., where the lumen is configured to form a more circular shape). In some embodiments, the stent 190 may comprise two or more anchor portions 210 extending from the main body stent end(s) 212.

In some embodiments, a stent 190 may additionally or alternatively comprise one or more mid-section anchor portions 210. For example, the stent 190 may comprise one or more anchor portions 210 extending from one or more positions along the length and/or about the radius of the main stent body 214.

Figure 21A:
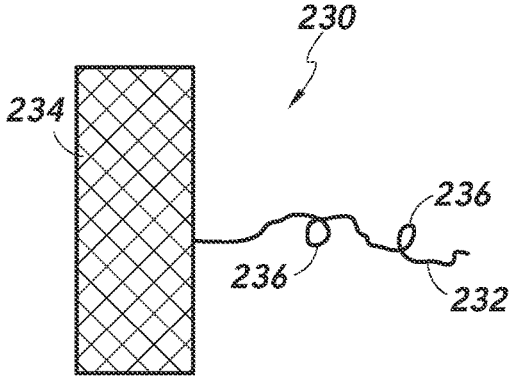
FIG. 21A depicts a stent comprising one or more wireforms configured to extend from the stent in accordance with one or more embodiments.

FIG. 21A depicts a stent 230 comprising one or more wireforms 232 (e.g., sutures) configured to extend from the stent 230. The wireforms 232 may be configured to extend from a stent main body 234 and/or may be configured to engage tissue (e.g., blood vessel walls) of various branching vessels/structures. For example, a wireform 232 may be at least partially composed of shape-memory material (e.g., Nitinol) and/or may be configured to form one or more loops 236 and/or other features configured to engage and/or secure to tissue.

Figure 21B:
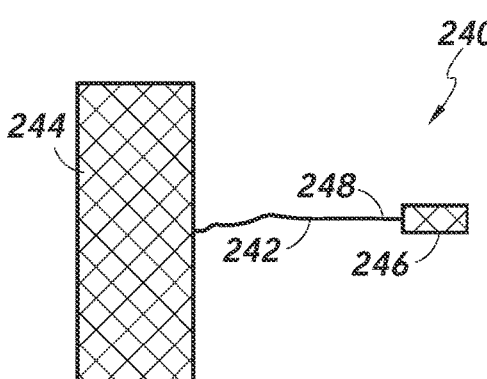
FIG. 21B depicts a stent comprising a wireform extending from a main stent body and/or a distal anchor attached at a distal end of the wireform in accordance with one or more embodiments.

FIG. 21B depicts a stent 240 comprising a wireform 242 extending from a main stent body 244 and/or a distal anchor 246 (e.g., an anchor stent) attached at a distal end 248 of the wireform 242. In some embodiments, the wireform 242 may be adjustable in length. For example, the wireform 242 may be configured to be secured via a sliding lock assembly to the main stent body 244, such that the wireform 242 length can be adjusted to create a desired tension pull between the distal anchor 246 and the main stent body 244 in order to secure the main stent body 244 at the desired location in a main blood vessel. For example, the wireform 242 may have a length of approximately 0.5 to 8 cm or longer, with a distal anchor 246 (e.g., an anchor stent) at the distal end 248 of the wireform 242. The distal anchor 246 may comprise an anchor stent forming a substantially tubular lumen and/or may have an expanded diameter sufficient for the anchor stent wall to engage a branch blood vessel wall (e.g., branching from the main blood vessel). For example, the expanded diameter of the distal anchor 246 may approximate the diameter of the branch blood vessel. The distal anchor 246 may have an expanded diameter of approximately 0.3 to 1 cm and/or a length of approximately 0.5 to 7 cm, although other lengths and diameters may be used depending on the particular application, such as the location where the distal anchor 246 is deployed (e.g., renal arteries, etc.).

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

Each element of each embodiment and its respective elements disclosed herein can be used with any other embodiment and its respective elements disclosed herein. All dimensions listed are by way of example, and devices according to the invention may have dimensions outside those specific values and ranges. The dimensions and shape of the device and its elements depend on the particular application. Unless otherwise noted, all technical and scientific terms used herein have the same meaning as commonly understood by one of ordinary skill in the art to which this disclosure belongs. In order to facilitate review of the various embodiments of the disclosure, the following explanation of terms is provided:

The singular terms "a", "an", and "the" include plural referents unless context clearly indicates otherwise. The term "or" refers to a single element of stated alternative elements or a combination of two or more elements, unless context clearly indicates otherwise. The term "includes" means "comprises." For example, a device that includes or comprises A and B contains A and B, but may optionally contain C or other components other than A and B. Moreover, a device that includes or comprises A or B may contain A or B or A and B, and optionally one or more other components, such as C.

The term "subject" refers to both human and other animal subjects. In certain embodiments, the subject is a human or other mammal, such as a primate, cat, dog, cow, horse, rodent, sheep, goat, or pig. In a particular example, the subject is a human patient.

Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

What is claimed is:

1. A stent comprising:
an elastically deformable stent frame lattice for increasing compliance and diastolic flow in a pulmonary artery, the stent frame lattice having a biased non-circular cross-sectional shape and being sized for placement in the pulmonary artery;
wherein the stent frame lattice is adapted to:
be percutaneously delivered into the pulmonary artery;
secure to a blood vessel wall of the pulmonary artery;
assume a biased first configuration characterized by a non-circular cross-sectional shape with inwardly-bowed minor-dimension sidewalls, a first major diameter, a first central minor diameter, and a first cross-sectional area;
upon deployment in the pulmonary artery, deform to a second configuration in response to diastolic pressure conditions, in which the stent frame lattice assumes an oval cross-sectional shape with outwardly-bowed minor-dimension sidewalls, a second major diameter, a second central minor diameter that is greater than the first central minor diameter, and a second cross-sectional area that is greater than the first cross-sectional area;
in response to systolic pressure conditions, transition to a third configuration in which the stent frame lattice assumes a third major diameter that is less than the second major diameter, a third central minor diameter that is greater than the second central minor diameter, and a third cross-sectional area that is greater than the second cross-sectional area; and
cycle between the second configuration and the third configuration within the pulmonary artery in response to cardiac cycling between diastolic and systolic phases.

2. The stent of claim 1, wherein the stent frame lattice comprises nitinol.

3. The stent of claim 1, further comprising one or more barbs extending radially outwardly from the stent frame lattice.

4. The stent of claim 1, wherein at least a portion of the stent frame lattice is adapted to be endothelialized into the blood vessel wall.

5. The stent of claim 1, wherein the stent frame lattice comprises a first stent layer and a second stent layer, wherein the first stent layer and the second stent layer comprise a single continuous layer of open-celled material, and the second stent layer is folded within the first stent layer such that the first stent layer comprises an outer layer of the stent frame lattice.

6. The stent of claim 5, wherein the stent frame lattice comprises a third stent layer, wherein the first stent layer and the second stent layer and the third stent layer comprise a single continuous layer of open-celled material, and the third stent layer is folded within the second stent layer such the third stent layer comprises an inner layer and the second stent layer is positioned between the first stent layer and the third stent layer.

7. The stent of claim 1, further comprising a tension line connecting a first side of the stent frame lattice to a second side of the stent frame lattice and extending across a lumen of the stent frame lattice along a minor dimension, the tension line being sized to physically hold the stent frame lattice in the biased first configuration or in the second configuration.

8. The stent of claim 7, wherein the tension line is at least partially composed of materials that dissolve within blood of a patient.

9. The stent of claim 8, wherein the tension line is sized to be percutaneously removed from the stent.

10. The stent of claim 7, wherein the tension line is a spring.

11. The stent of claim 1, wherein the non-circular cross-sectional shape has a constant angular orientation along a length of the stent frame lattice.

12. The stent of claim 1, further comprising one or more anchors extending from the stent frame lattice and sized to be deployed into engagement with tissue of a branch blood vessel that branches away from, and has a smaller diameter than, the pulmonary artery.

13. The stent of claim 1, further comprising a lining extending along the stent frame lattice to prevent flow of blood through the stent frame lattice.

14. A system for providing compliance to a pulmonary artery, the system comprising:
a catheter comprising a catheter distal portion sized to be percutaneously advanced within a patient's vasculature to a pulmonary artery; and
a stent releasably secured to the catheter distal portion and comprising an elastically deformable stent frame lattice having a biased non-circular cross-sectional shape and being sized for placement in the pulmonary artery, the elastically deformable stent frame lattice forming a lumen extending between a first opening and a second opening of the stent frame lattice;
wherein the stent frame lattice is adapted to:
be percutaneously delivered into the pulmonary artery;
secure to a blood vessel wall of the pulmonary artery;
assume a biased first configuration outside a body of the patient, the biased first configuration defining an inner flow lumen characterized by a non-circular cross-sectional shape with inwardly-bowed minor-dimension sidewalls, the non-circular cross-sectional shape having a constant angular orientation along a length of the stent frame lattice and defining a first major diameter along a major dimension, a first central minor diameter along a minor dimension, and a first cross-sectional area;

upon deployment in the pulmonary artery, deform to a second configuration in response to diastolic pressure conditions, in which the stent frame lattice assumes an oval cross-sectional shape with outwardly-bowed minor-dimension sidewalls, a second major diameter, a second central minor diameter that is greater than the first central minor diameter, and a second cross-sectional area that is greater than the first cross-sectional area; and in response to systolic pressure conditions, transition to a third configuration in which the stent frame lattice assumes a third major diameter along the major dimension that is less than the second major diameter, a third central minor diameter along the minor dimension that is greater than the second central minor diameter, and a third cross-sectional area that is greater than the second cross-sectional area, wherein the stent comprises a tension line connecting a first side of the stent frame lattice to a second side of the stent frame lattice and extending across the inner flow lumen along the minor dimension, the tension line being sized to physically hold the stent frame lattice temporarily in the biased first configuration or the second configuration.

15. The system of claim 14, wherein the catheter distal portion comprises an expandable balloon sized to cause the stent frame lattice to radially expand.

16. The system of claim 14, wherein the catheter distal portion comprises a retractable sheath adapted to prevent the stent frame lattice from radially expanding to the second configuration.

17. A device for providing compliance within a blood vessel, the device comprising:

a distal stent segment sized for placement in a blood vessel;

a proximal stent segment;

an elastically deformable middle stent segment positioned between the distal stent segment and the proximal stent segment, the middle stent segment being adapted to:

assume a biased first configuration outside of a body in which the middle stent segment has a non-circular cross-sectional shape with inwardly-bowed minor-dimension sidewalls, the non-circular cross-sectional shape defining a first major diameter along a major dimension, a first central minor diameter along a minor dimension, and a first cross-sectional area;

in response to diastolic pressure conditions within the blood vessel, transition to a second configuration in which the middle stent segment assumes an oval cross-sectional shape with outwardly-bowed minor-dimensional sidewalls, a second major diameter, a second central minor diameter that is greater than the first central minor diameter, and a second cross-sectional area that is greater than the first cross-sectional area; and in response to systolic pressure conditions within the blood vessel, transition to a third configuration in which the middle stent segment assumes a third major diameter along the major dimension that is less than the second major diameter, a third central minor diameter along the minor dimension that is greater than the second central minor diameter, and a third cross-sectional area that is greater than the second cross-sectional area; and a lining extending along the middle stent segment to prevent flow of blood through cells of the middle stent segment, the lining not extending along open cells of the distal stent segment or the proximal stent segment.

18. The device of claim 17, wherein the distal stent segment and the proximal stent segment are sized to be radially expanded into contact with an aortic wall of an aorta, and wherein the third cross-sectional area of the middle stent approximates a cross-sectional area of the aorta.

19. The device of claim 17, wherein the first major diameter is greater than the second major diameter.

20. The device of claim 17, wherein the distal stent segment and the proximal stent segment comprise a plastically deformable material.

21. The device of claim 20, wherein the distal stent segment and the proximal stent segment comprise stainless steel or a cobalt alloy, and the middle stent segment comprises nitinol.

22. The device of claim 17, wherein the non-circular cross-sectional shape is a peanut shape.

23. The device of claim 17, wherein the non-circular first cross-sectional shape is a kidney shape.

24. A method of restoring compliance to a pulmonary artery, the method comprising:

providing a stent having a biased first configuration having a non-circular cross-sectional shape with inwardly-bowed minor-dimensional sidewalls, a first major diameter, a first central minor diameter, and a first cross-sectional area;

deploying the stent in the pulmonary artery such that diastolic pressure forces cause the stent to deform to a second configuration having an oval cross-sectional shape with outwardly-bowed minor-dimensional sidewalls, a second major diameter, a second central minor diameter that is greater than the first central minor diameter, and a second cross-sectional area that is greater than the first cross-sectional area;

increasing flow in the pulmonary artery by allowing the stent to respond to systolic pressure forces by transitioning from the second configuration to a third configuration having a more circular cross-sectional shape including a third major diameter that is less than the first and second major diameters, a third central minor diameter that is greater than the second central minor diameter, and a third cross-sectional area that is greater than the second cross-sectional area; and cycling the stent between the second configuration and the third configuration in response to cyclically-changing luminal forces of the pulmonary artery on the stent to restore compliance to the pulmonary artery.

25. The method of claim 24, deploying the stent involves expanding an expandable balloon within a lumen of the stent.

26. The method of claim 25, wherein the stent is advanced through vasculature of a patient positioned on the expandable balloon.

27. The method of claim 24, slidingly positioning a sheath over the stent.

28. The method of claim 24, wherein after radially expanding deploying the stent, the stent is physically held by a restraint connecting a first side of the stent to a second side of the stent and extending across an inner flow lumen of the stent and sized to restrain the stent in the biased first configuration or in the second configuration.

29. The method of claim 28, wherein the method further comprises, releasing the restraint from the stent so that the stent is no longer held in the biased first configuration or in the second configuration, and can deform between the second configuration and the third configuration.

30. The method of claim 29, wherein the restraint comprises a tension line, and wherein releasing the restraint involves cutting the tension line.

31. The method of claim 29, wherein the restraint comprises an absorbable tension line, and wherein releasing the restraint occurs responsive to exposure of the absorbable tension line to blood.

32. The method of claim 24, wherein the non-circular cross-sectional shape has a constant angular orientation along a length of the stent.

33. The method of claim 24, wherein the stent further comprises one or more anchors extending from the stent, the method further comprising deploying the one or more anchors into engagement with tissue of a branch blood vessel that branches away from, and has a smaller diameter than, the pulmonary artery.

34. The method of claim 24, wherein the stent further comprises a lining extending along the stent to prevent flow of blood through a frame of the stent.

35. A device for restoring pulmonary artery compliance, comprising:

a stent body comprising an elastically deformable stent frame lattice sized for placement in a pulmonary artery, wherein the stent frame lattice is adapted to:

assume a biased first configuration defining a non-circular cross-sectional shape with inwardly-bowed minor-dimension sidewalls, the non-circular cross-sectional shape having a constant angular orientation along a length of the stent frame lattice and defining a first major diameter along a major dimension, a first central minor diameter along a minor dimension, and a first cross-sectional area;

upon deployment in the pulmonary artery, deform to a second configuration in response to diastolic pressure conditions, in which the stent frame lattice assumes an oval cross-sectional shape with outwardly-bowed minor-dimensional sidewalls, a second major diameter, a second central minor diameter that is greater than the first central minor diameter, and a second cross-sectional area that is greater than the first cross-sectional area; and in response to increasing luminal forces of the pulmonary artery on the stent frame lattice associated with systolic pressure conditions, transition to a third configuration in which the stent frame lattice assumes a third major diameter that is less than the second major diameter, a third central minor diameter that is greater than the second central minor diameter, and a third cross-sectional area that is greater than the second cross-sectional area; and one or more anchors extending from the stent body and sized to be deployed into engagement with tissue of a branch blood vessel that branches away from, and has a smaller diameter than, the pulmonary artery.

36. The device of claim 35, wherein at least one of the one or more anchors extends from the stent body at a position between a first opening and a second opening of the stent body.

37. The device of claim 35, wherein at least one of the one or more anchors extends from at or near a first opening of the stent body.

38. The device of claim 35, wherein at least one of the one or more anchors comprises a wireform adapted to pass within the branch blood vessel and sized to engage wall tissue of the branch blood vessel.

39. The device of claim 38, wherein the wireform comprises a shape-memory material.

40. The device of claim 35, wherein at least one of the one or more anchors comprises an anchor stent body wherein the anchor stent body is sized to be radially expanded into contact with a wall of the branch blood vessel.

41. The device of claim 40, wherein the anchor stent body comprises a shape-memory material and is biased toward a configuration wherein the anchor stent body has the non-circular cross-sectional shape.

42. The device of claim 40, wherein the anchor stent body has an anchor stent body length between 0.5 and 7 cm.

* * * * *